(12) United States Patent
Shao et al.

(10) Patent No.: US 10,407,413 B2
(45) Date of Patent: Sep. 10, 2019

(54) METHOD FOR PREPARING PYRAZOLECARBOXYLIC ACID DERIVATIVE, AND INTERMEDIATE THEREOF

(71) Applicant: ZHEJIANG YONGTAI TECHNOLOGY CO., LTD, Linhai Zone, Zhejiang (CN)

(72) Inventors: Hongming Shao, Zhejiang (CN); Renbao He, Zhejiang (CN); Yizhong Jin, Zhejiang (CN); Lei Wang, Zhejiang (CN)

(73) Assignee: ZHEJIANG YONGTAI TECHNOLOGY CO., LTD., Linhai Zone, Zhejiang (CN)

( * ) Notice: Subject to any disclaimer, the term of this patent is extended or adjusted under 35 U.S.C. 154(b) by 0 days.

(21) Appl. No.: 15/737,483

(22) PCT Filed: Jun. 15, 2016

(86) PCT No.: PCT/CN2016/085814
§ 371 (c)(1),
(2) Date: Dec. 18, 2017

(87) PCT Pub. No.: WO2016/202254
PCT Pub. Date: Dec. 22, 2016

(65) Prior Publication Data
US 2018/0194753 A1    Jul. 12, 2018

(30) Foreign Application Priority Data

Jun. 19, 2015 (CN) .......................... 2015 1 0346308
Jun. 19, 2015 (CN) .......................... 2015 1 0348921

(51) Int. Cl.
| | | |
|---|---|---|
| C07D 405/04 | (2006.01) | |
| C07D 231/14 | (2006.01) | |
| C07C 251/12 | (2006.01) | |
| C07C 251/14 | (2006.01) | |
| C07D 231/12 | (2006.01) | |
| C07C 221/00 | (2006.01) | |
| C07C 225/14 | (2006.01) | |
| C07D 251/30 | (2006.01) | |
| C07C 49/255 | (2006.01) | |
| C07D 295/125 | (2006.01) | |
| C07B 33/00 | (2006.01) | |

(52) U.S. Cl.
CPC .......... *C07D 405/04* (2013.01); *C07C 49/255* (2013.01); *C07C 221/00* (2013.01); *C07C 225/14* (2013.01); *C07C 251/12* (2013.01); *C07C 251/14* (2013.01); *C07D 231/12* (2013.01); *C07D 231/14* (2013.01); *C07D 251/30* (2013.01); *C07D 295/125* (2013.01); *C07B 33/00* (2013.01)

(58) Field of Classification Search
None
See application file for complete search history.

(56) References Cited

FOREIGN PATENT DOCUMENTS

| | | |
|---|---|---|
| CN | 101044116 | 9/2007 |
| CN | 101796021 | 8/2010 |
| CN | 103787977 | 5/2014 |
| CN | 104254523 | 12/2014 |
| CN | 105541716 | 5/2016 |
| JP | 2000-044541 | 2/2000 |
| WO | WO 2015/040352 | 3/2015 |

OTHER PUBLICATIONS

International Search Report of PCT/CN2016/085814, dated Sep. 1, 2016, 6 pages.

*Primary Examiner* — Kamal A Saeed
(74) *Attorney, Agent, or Firm* — Nixon & Vanderhye P.C.

(57) ABSTRACT

Provided are a preparation method for synthesizing a pyrazolecarboxylic acid derivative of the following formula (I), which is suitable for industrial production, and an intermediate as shown by the following formula (II). The method is high in reaction yield in each step, low in waste gas and waste water and low in cost, and requires no special reaction equipment.

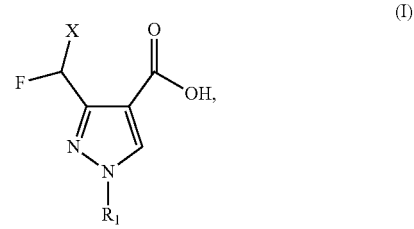

(I)

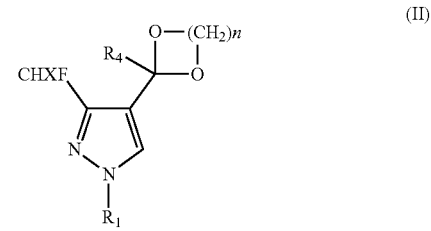

(II)

20 Claims, 9 Drawing Sheets

METHOD FOR PREPARING PYRAZOLECARBOXYLIC ACID DERIVATIVE, AND INTERMEDIATE THEREOF

This application is the U.S. national phase of International Application No. PCT/CN2016/085814 filed Jun. 15, 2016, which designated the U.S. and claims priority to CN Patent Application No. 201510346308.6 filed Jun. 19, 2015 and CN Patent Application No. 201510348921.1 filed Jun. 19, 2015, the entire contents of each of which are hereby incorporated by reference.

TECHNICAL FIELD

The present invention relates to a method for preparing pyrazolecarboxylic acid derivatives and its intermediates.

BACKGROUND ART

Pyrazolecarboxylic acid derivative, such as 3-difluoromethyl-1-methyl-1H-pyrazole-4-carboxylic acid, is the key intermediate in the preparation of fungicides.

Document JP-2000-044541 reports that, in the presence of a base, the corresponding substituted pyrazoles with carboxylic acid dialkyl esters such as dimethyl sulfate, diethyl sulfate were N-methylated to give N-substituted pyrazole, and then after a series of reaction to give pyrazolecarboxylic acid derivatives. However, because of the toxicity of dialkyl sulfate, it is difficult to apply this preparation process on a large scale.

China Patent CN101044116A provides a preparation process that uses trialkylphosphate in place of virulent dialkyl sulfate. Yet this preparation process requires an 18-24 hours reaction under 180-200° C. high temperature. Moreover, it produces large amounts of waste water in the process of post-processing, which makes it do not fulfill the environmental requirements.

JACS, 73,3684 (1951) describes that, (2-ethoxy-methylene)-4,4-difluoro-methyl ethyl acetoacetate, which was obtained by reacting ethyl 4,4-difluoro-3-oxobutyrate with triethyl orthoformate and acetic anhydride, and then was reacted with a hydrazine derivative to give 3-difluoromethyl-1-methyl-1H-pyrazole-4-carboxylic acid ethyl ester, which then was hydrolyzed to give the corresponding hydrolysis product. However, ethyl 4,4-difluoro-3-oxobutyrate is expensive and the yield of this method is less than 70%.

As introduced above, the prior art of preparation process of pyrazolecarboxylic acid derivative exists many issues, such as the use of toxic materials, the difficulty of waste treatment resulted in environmental pollution.

DISCLOSURE OF THE INVENTION

For the above-mentioned problems in the prior art, an technical problem to be solved by the present invention is to provide a simple, economical and environmental friendly preparation method for preparing pyrazolecarboxylic acid derivatives. Due to utilizing novel intermediates, the method is high in reaction yield in each step, low in waste gas and waste water and low in cost, and requires no special reaction equipment.

According to the present invention, the above object is achieved by the following embodiments.

According to an embodiment of the present invention, the present invention provides a compound of formula (II),

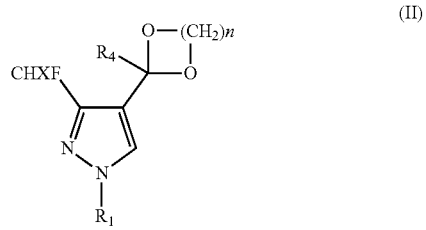

(II)

wherein,
$R_1$ is methyl or ethyl, preferably methyl;
$R_4$ is hydrogen or methyl, preferably methyl:
n is 0-4, preferably 0 or 1;
X is F, Cl or $CF_3$, preferably F.

According to an embodiment of the present invention, $R_1$ is methyl, $R_4$ is methyl n is 1, X is F.

According to an embodiment of the present invention. $R_1$ is ethyl, $R_4$ is hydrogen, n is 1, X is F.

According to an embodiment of the present invention. $R_1$ is methyl, $R_4$ is hydrogen, n is 1, X is F.

According to an embodiment of the present invention, $R_1$ is methyl, $R_4$ is methyl, n is 0, X is F.

According to an embodiment of the present invention. $R_1$ is ethyl, $R_4$ is hydrogen, n is 0, X is F.

According to an embodiment of the present invention. $R_1$ is methyl, $R_4$ is hydrogen, n is 0, X is F.

According to an embodiment of the present invention, when n=0 in the compound of formula (II), the corresponding compound of formula (II) is as follow:

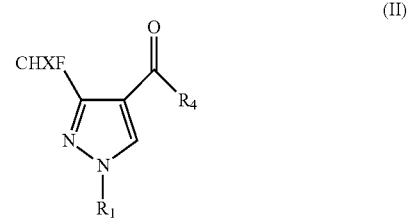

(II)

wherein, $R_1$ is methyl or ethyl, preferably methyl; $R_4$ is hydrogen or methyl, preferably methyl.

According to an embodiment of the present invention, the present invention provides a method for preparing the compound of the above formula (II), said method comprising the following steps of:

(1) in the presence of Lewis acid, reacting α-fluoride amine of formula (III) with ethylene derivative of formula (IV) to obtain vinamidinium salt of formula (V) (i.e. 1,5-diaza-pentadiene salt), said α-fluoride amine of formula (III) is as follows:

(III)

wherein, X is defined as described previously, and $R_2$ and $R_3$ are independently selected from $C_1$-$C_4$ alkyl, preferably methyl:

said ethylene derivative of formula (IV) is as follows:

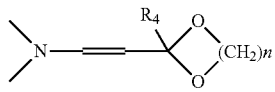

(IV)

wherein, $R_4$ is hydrogen or methyl, preferably methyl, and n is 0-1, preferably 0 or 1;

particularly, when n=0, the corresponding ethylene derivative of formula (IV) is as follows:

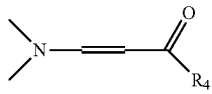

(IV)

wherein, $R_4$ is hydrogen or methyl;

said 1,5-diaza-pentadiene salt of formula (V) is as follows:

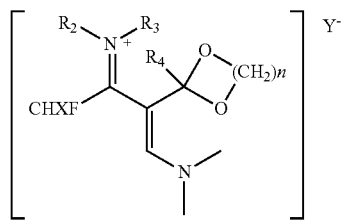

(V)

wherein, n, $R_2$, $R_3$, and $R_4$ are defined as described previously, and $Y^-$ is an anion, wherein said anion is selected from $[BF_4]^-$, $[AlCl_3F]^-$, $[AlF_4]^-$, $[ZnCl_2F]^-$, $[SbF_6]^-$, $[SnCl_4F]^-$, $[BiCl_3F]^-$, $[GaCl_3F]^-$ and $[SiCl_4F]^-$, which are derived from the corresponding Lewis acids;

particularly, when n=0, the corresponding 1,5-diaza-pentadiene salt of formula (V) is as follows:

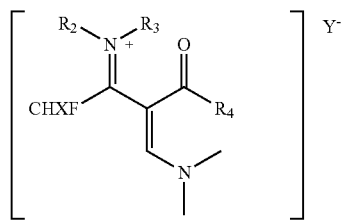

(V)

wherein, the definitions of $R_2$, $R_3$, $R_4$ and $Y^-$ are as described previously;

(2) reacting the 1,5-diaz-pentadiene salt of formula (V) with hydrazine to obtain the compound of formula (II).

According to an embodiment of the present invention, the present invention provides a method for preparing the compound of the following formula (I),

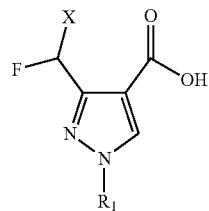

(I)

wherein, $R_1$ is methyl or ethyl, preferably methyl:

X is F, Cl or $CF_3$, preferably F:

said method comprising the following steps of:

(1) in the presence of Lewis acid, reacting α-fluoride amine of formula (III) with ethylene derivative of formula (IV) to obtain vinamidinium salt of formula (V) (i.e. 1,5-diaza-pentadiene salt), said α-fluoride amine of formula (III) is as follows:

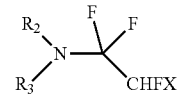

(III)

wherein, X is defined as described previously, and $R_2$ and $R_3$ are independently selected from $C_1$-$C_4$ alkyl, preferably methyl;

said ethylene derivative of formula (IV) is as follows:

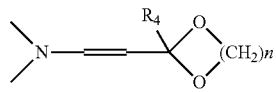

(IV)

wherein, $R_4$ is hydrogen or methyl, preferably methyl, and n is 0-1, preferably 0 or 1;

particularly, when n=0, the corresponding ethylene derivative of formula (IV) is as follows:

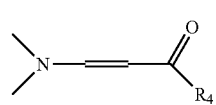

(IV)

wherein, $R_4$ is hydrogen or methyl, preferably methyl;

said 1,5-diaza-pentadiene salt of formula (V) is as follows:

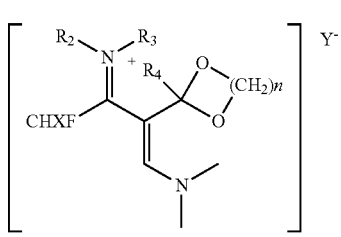

(V)

wherein, the definitions of n, $R_2$, $R_3$, and $R_4$ are as described previously, and $Y^-$ is an anion, wherein said anion is selected from $[BF_4]^-$, $[AlCl_3F]^-$, $[AlF_4]^-$, $[ZnCl_2F]^-$, $[SbF_6]^-$, $[SnCl_4F]^-$, $[BiCl_3F]^-$, $[GaCl_3F]$ and $[SiCl_4F]^-$, which are derived from the corresponding Lewis acids;

particularly, when n=0, the corresponding 1,5-diaza-pentadiene salt of formula (V) is as follows:

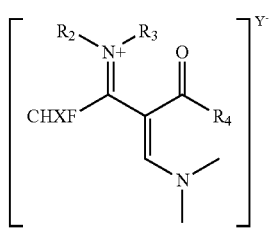

(V)

wherein, the definitions of $R_2$, $R_3$, $R_4$ and $Y^-$ are as described previously.

(2) reacting the 1,5-diaz-pentadiene salt of formula (V) with hydrazine to obtain the compound of formula (II), said compound of formula (II is as follows:

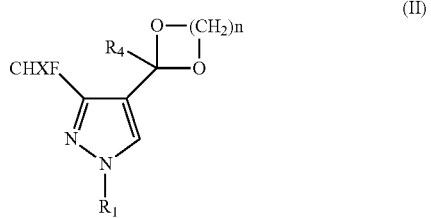

(II)

wherein, the definitions of X, n, $R_1$ and $R_4$ are as described previously;

particularly, when n=0, the corresponding compound of formula (II) is as follows:

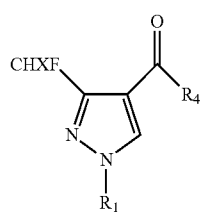

(II)

wherein, the definitions of X, $R_1$ and $R_4$ are as described previously;

(3) hydrolyzing and oxidizing one of the compounds of formula (II) with n=1-4, or oxidizing one of the compounds of formula (II) with n=0, to obtain the compound of formula (I).

According to an embodiment of the present invention, the Lewis acid in step (1) is selected from the following compounds: $BF_3$, $AlCl_3$, $AlF_3$, $ZnCl_2$, $PF_5$, $SbF_5$, $SnCl_4$, $BiCb_3$, $GaCl_3$ and $SiCl_4$, preferably $BF_3$.

According to an embodiment of the present invention, the reaction temperature in step (1) is around −20° C. to 60° C., preferably around −10° C. to 40° C., and more preferably around 0° C.-to 30° C. For economic reasons, the reaction in step (1) is carried out at room temperature preferably.

According to an embodiment of the present invention, the α-fluoride amine used in step (1) is selected from 1,1,2,2-tetrafluoro-ethyl-N,N-dimethylamine, 1,1,2,2-tetrafluoro-ethyl-N,N-diethylamine, 1,1,2-trifluoro-2-(trifluoromethyl) ethyl-N,N-dimethylamine, 1,1,2-trifluoro-2-(trifluoromethyl)ethyl-N,N-diethylamine, 1,1,2-trifluoro-2-chloroethyl-N,N-dimethylamine and 1,1,2-trifluoro-2-chloroethyl-N,N-diethylamine, preferably selected from 1,1,2,2-tetrafluoro-ethyl-N,N-dimethylamine and 1,1,2,2-tetrafluoro-ethyl-N,N-diethylamine, and more preferably selected from 1,1,2,2-tetrafluoro-ethyl-N,N-dimethylamine.

The amount of the Lewis acid used is not particularly limited. According to an embodiment of the present invention, the molar ratio of the Lewis acid and the α-fluoride amine in step (1) is 1:1 to 10:1, preferably 1:1 to 5:1, and more preferably 1:1 to 1.3:1; the molar ratio of the α-fluoride amine and the ethylene derivative is 1:10 to 10:1, preferably 1:5 to 5:1, and more preferably 1.3:1 to 1:1.3.

According to an embodiment of the present invention, the reaction in step (2) of the above method is carried out in the presence of solvent. The suitable solvent, for example, is selected from aliphatic and aromatic hydrocarbons, such as hexane, cyclohexane, benzene or toluene. Or the suitable solvent is selected from aliphatic and aromatic hydrocarbons that are substituted by fluorine and chlorine, such as methylene chloride, dichloromethane, chloroform, carbon tetrachloride, fluorobenzene, chlorobenzene or dichlorobenzenes. Besides, ether can be used as the suitable solvent, for example, diethyl ether, diphenyl ether, methyl tert-butvl ether, isopropyl ethyl ether, dioxane, diethylene glycol dimethyl ether, dimethyl ethylene glycol or THF. Nitrile may also be used as the suitable solvent, such as, methyl nitrile, butvronitrile or benionitrile. Said solvent is preferably selected from diethyl ether, acetonitrile, methylene chloride and tetrahydrofuran, and more preferably acetonitrile or tetrahydrofuran.

According to an embodiment of the present invention, the hydrazine used in step (2) is methylhydrazine or ethylhydrazine, preferably methylhydrazine.

According to an embodiment of the present invention, the molar ratio of the 1,5-diaza-pentadiene salt of formula (V) and the aforementioned hydrazine in step (2) is 1:10 to 10:1, preferably 1:5 to 5:1, and more preferably 1.3:1 to 1:1.3.

According to an embodiment of the present invention the reaction temperature in step (2) is around −20° C. to 60° C., preferably around −10 to 40° C., and more preferably around 0° C. to 30° C. For economic reasons, the reaction in step (2) in the reaction is carried out at room temperature preferably.

According to an embodiment of the present invention, the hydrolysis reaction of the compounds of formula (II) in step (3) is carried out in the presence of a solvent, and the solvent used for the hydrolysis reaction is selected from a mixture of methanol ethanol, acetonitrile or tetrahydrofuran etc., with water, or using water alone as a solvent, preferably using water.

According to an embodiment of the present invention, the hydrolysis reaction can be carried out under basic or acidic conditions, preferably under acidic condition. The acid used for hydrolysis reaction can be organic or inorganic acid, preferably inorganic acid. The inorganic acid can be hydrochloric acid, sulfuric acid, hydrobromic acid, or phosphoric acid etc., preferably hydrochloric acid or sulfuric acid. The hydrolysis reaction temperature can be around 30° C. to 100° C., preferably around 30° C. to 70° C., and more preferably around 50 T to 60° C. When the hydrolysis reaction is carried out in the presence of acid, the molar ratio of compound of formula (II) and the acid can be an excess of acid, such molar ratio is as 1:2 to 1:10, preferably 1:3 to 1:5, and more preferably 1:2 to 1:3.

According to an embodiment of the present invention, the oxidizing agent used in the oxidation reaction can be hydrogen peroxide, sodium hypochlorite, potassium permanganate, sodium chlorate, or potassium chlorate, etc., preferably hydrogen peroxide or sodium hypochlorite. In the oxidation reaction, the oxidizing agent is used in excess.

According to an embodiment of the present invention, the oxidation reaction is carried out in the same solvent that is used in the hydrolysis reaction, and said solvent is selected from mixture of methanol, ethanol, acetonitrile, or tetrahydrofuran etc., with water, or using water alone as a solvent, preferably using water.

According to an embodiment of the present invention, the hydrolysis reaction and the oxidation reaction are continuously carried out, and based on the mole of compound of formula (II), the oxidizing agent is used in an amount of 1:2 to 1:10 moles, preferably 13 to 1:5 moles, and more preferably 1:2 to 1:3 moles. In the oxidation reaction, the reaction temperature may be around 30° C. to 100° C., preferably around 50° C. to 100° C., and more preferably around 70° C. to 100° C.

DETAILED DESCRIPTION OF THE PREFERRED EMBODIMENT

Figure 1:
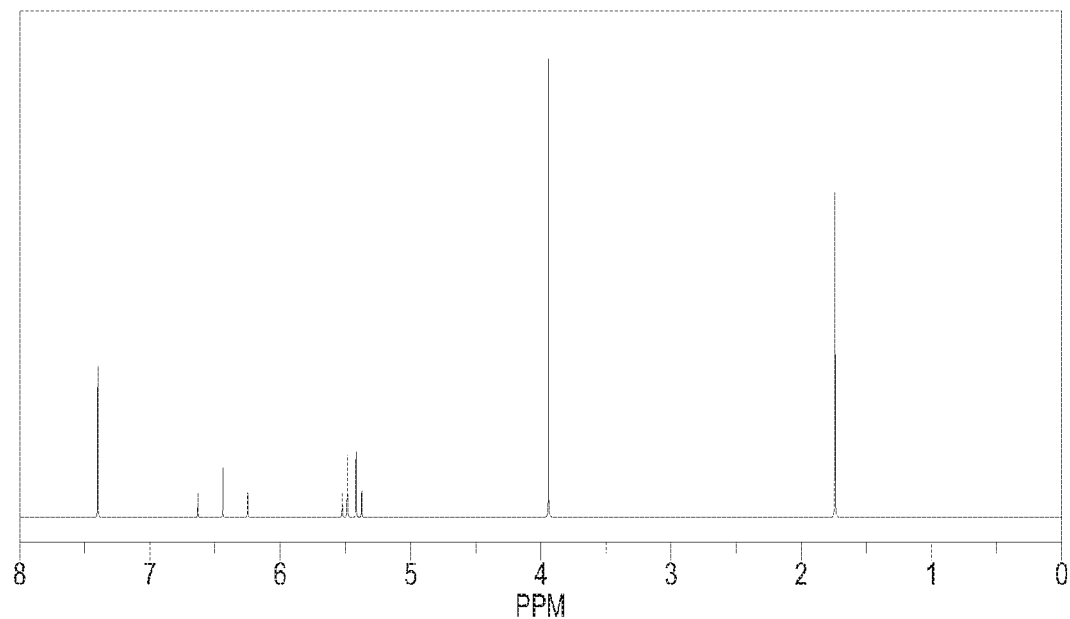
FIG. 1: $^1$H NMR spectrum of 3-(difluoromethyl)-1-methyl-4-(2-methyl-1,3-dioxetan-2-yl)-1H-pyrazole.
Figure 2:
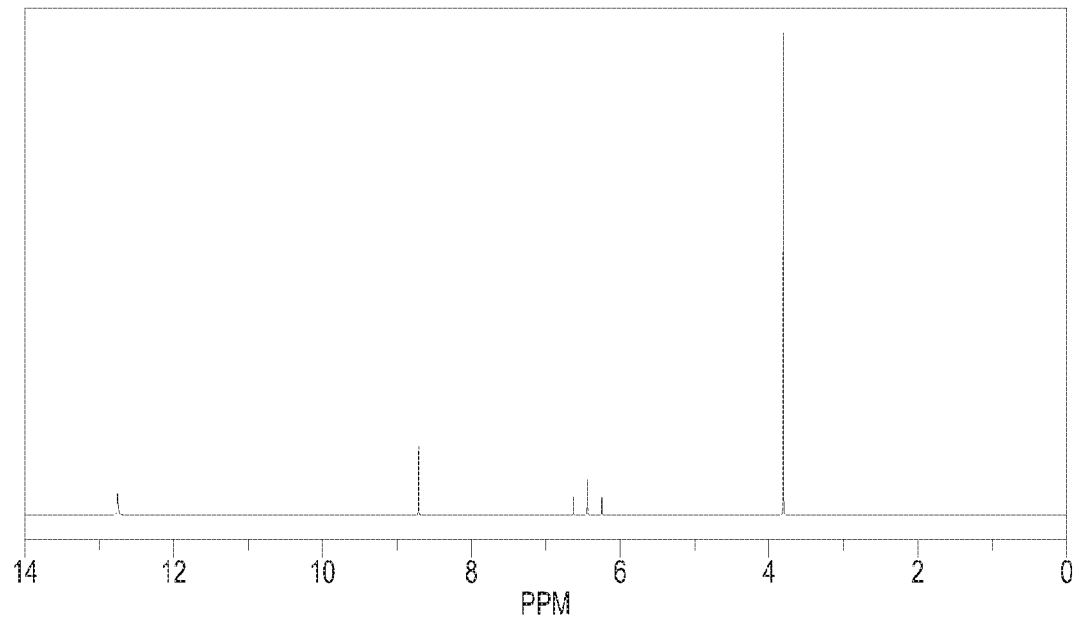
FIG. 2: $^1$H NMR spectrum of 3-(difluoromethyl)-1-methyl-1H-pyrazole-4-carboxylic acid.
Figure 3:
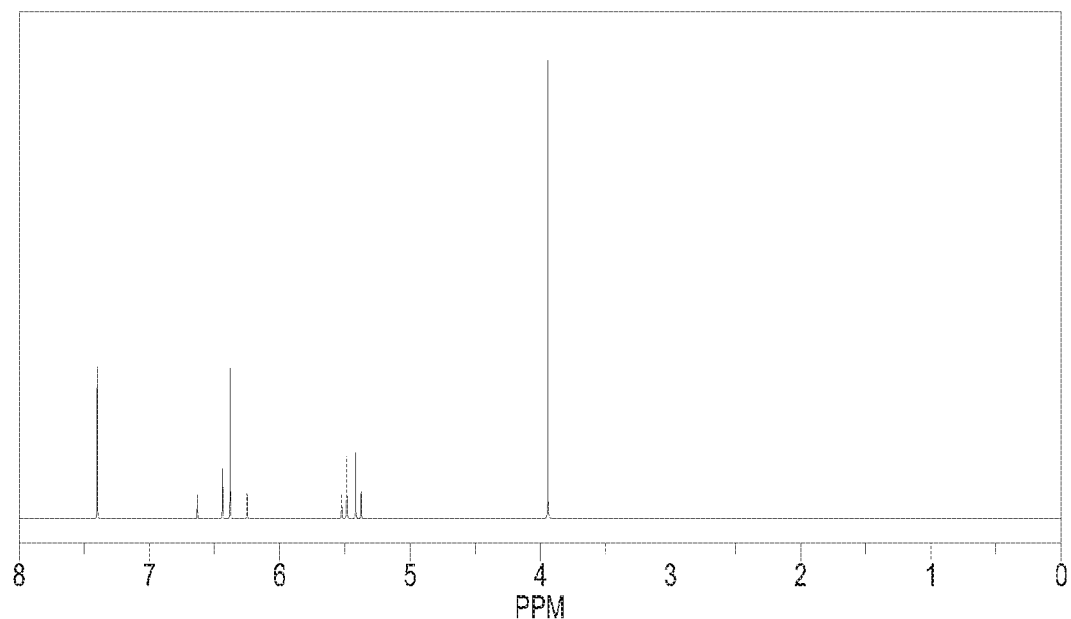
FIG. 3: $^1$H NMR spectrum of 3-(difluoromethyl)-1-methyl-4-(1,3-dioxetan-2-yl)-1H-pyrazole.
Figure 4:
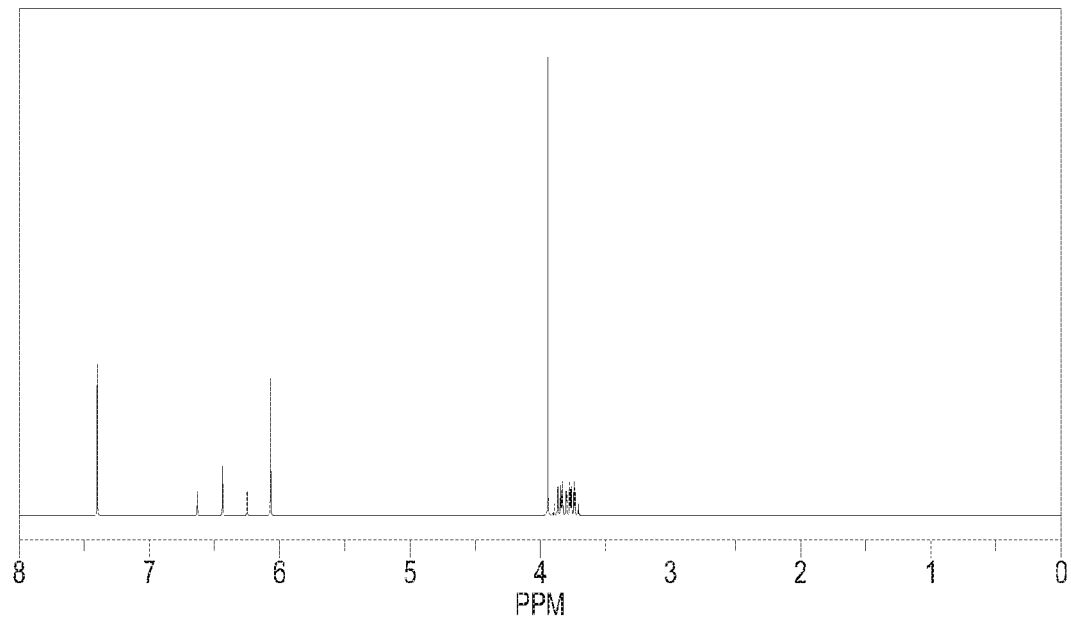
FIG. 4: $^1$H NMR spectrum of 3-(difluoromethyl)-1-methyl-4-(1,3-dioxolan-2-yl)-1H-pyrazole.
Figure 5:
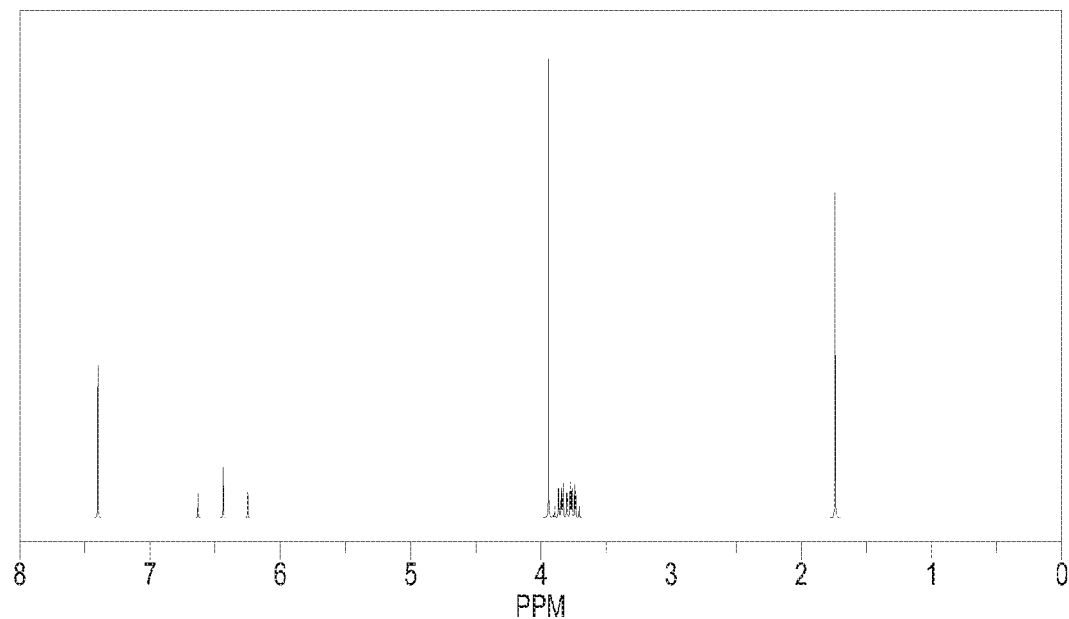
FIG. 5: $^1$H NMR spectrum of 3-(difluoromethyl)-1-methyl-4-(2-methyl-1,3-dioxolan-2-yl)-1H-pyrazole.
Figure 6:
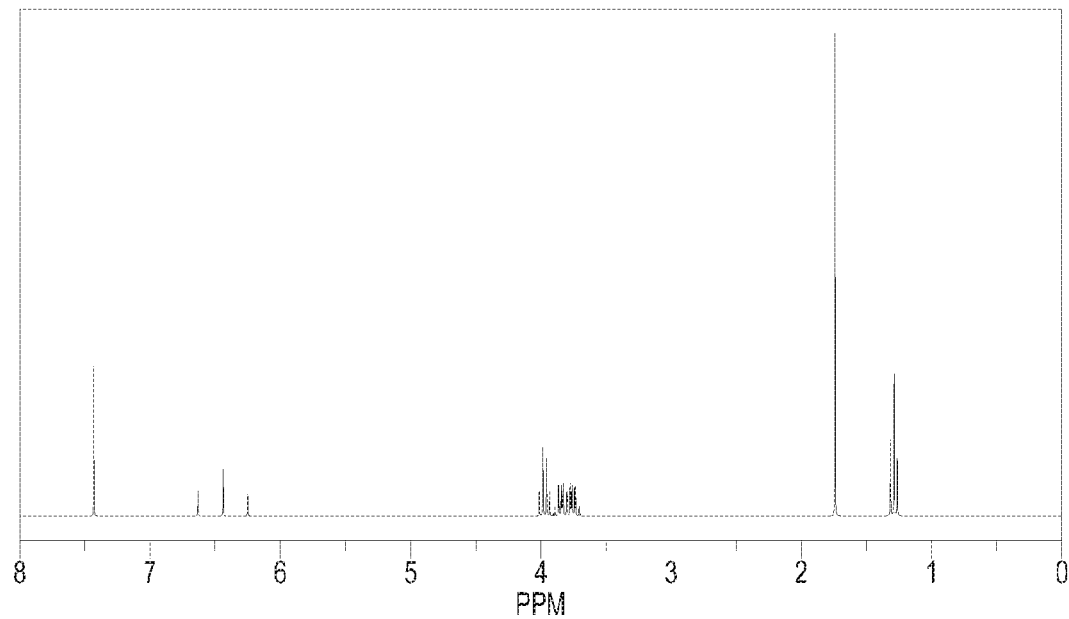
FIG. 6: $^1$H NMR spectrum of 3-(difluoromethyl)-1-ethyl-4-(2-methyl-1,3-dioxolan-2-yl)-1H-pyrazole.
Figure 7:
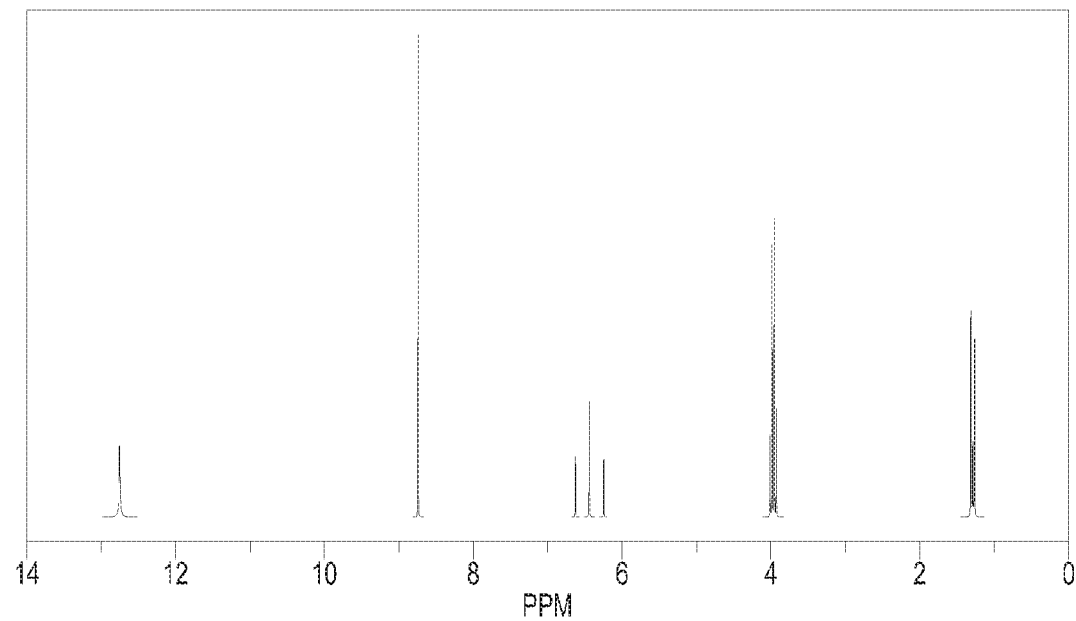
FIG. 7: $^1$H NMR spectrum of 3-(difluoromethyl)-1-ethyl-1H-pyrazole-4-carboxylic acid.
Figure 8:
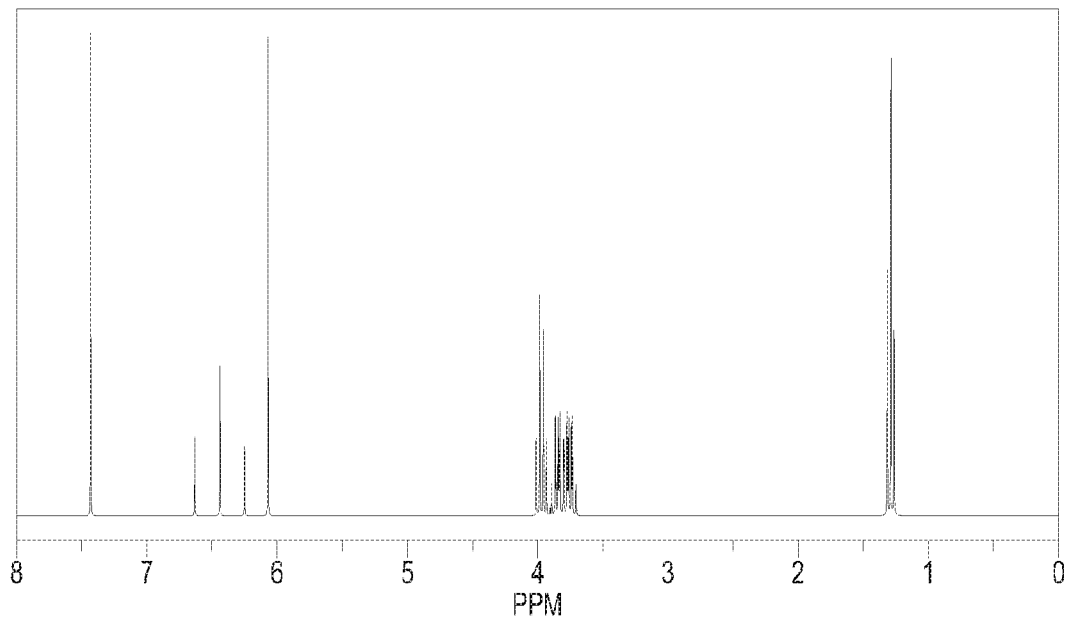
FIG. 8: $^1$H NMR spectrum of 3-(difluoromethyl)-1-ethyl-4-(1,3-dioxolan-2-yl)-1H-pyrazole.
Figure 9:
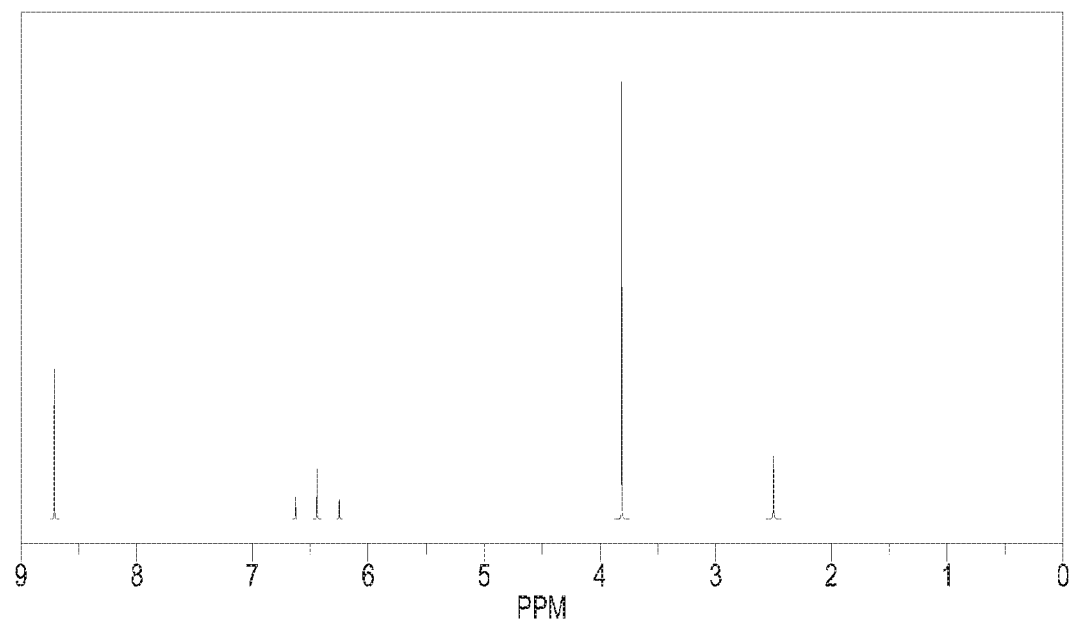
FIG. 9: $^1$H NMR spectrum of 1-(3-(difluoromethyl)-1-methyl-1H-pyrazol-4-yl)ethanone.
Figure 10:
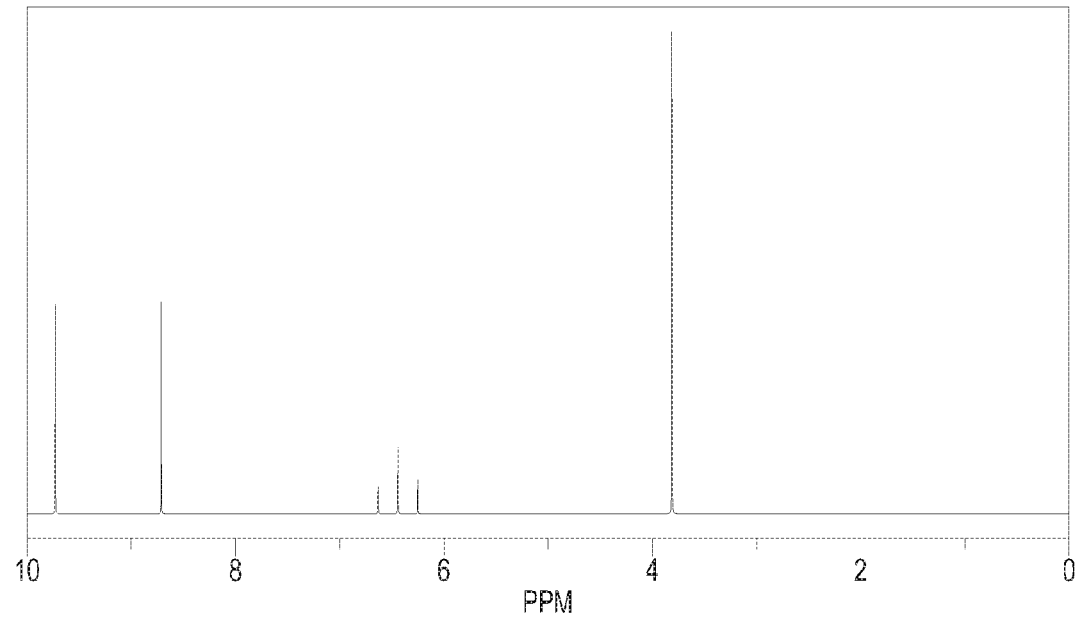
FIG. 10: $^1$H NMR spectrum of 3-(difluoromethyl)-1-methyl-1H-pyrazole-4-acetaldehyde.
Figure 11:
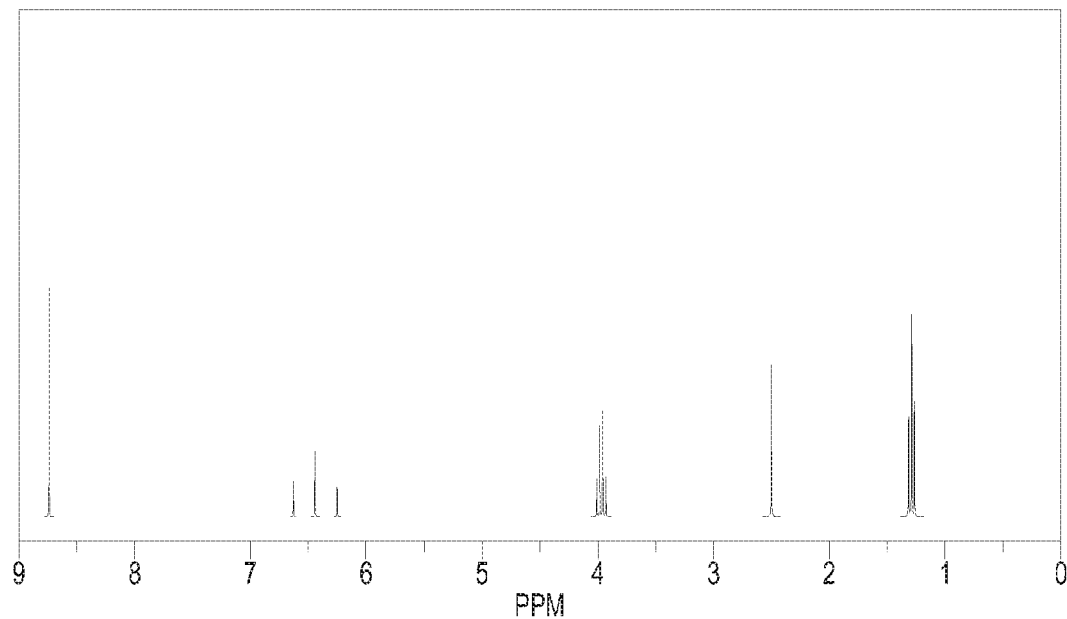
FIG. 11: $^1$H NMR spectrum of 1-(3-(difluoromethyl)-1-ethyl-1H-pyrazol-4-yl)ethanone.
Figure 12:
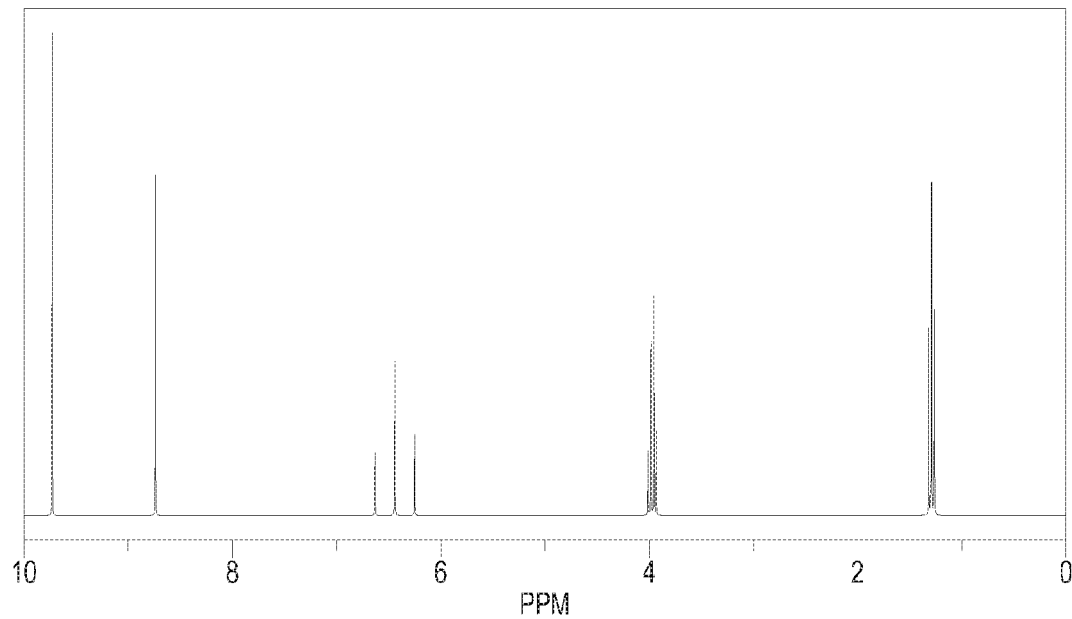
FIG. 12: $^1$H NMR spectrum of 3-(difluoromethyl)-1-methyl-1H-pyrazole-4-acetaldehyde.
Figure 13:
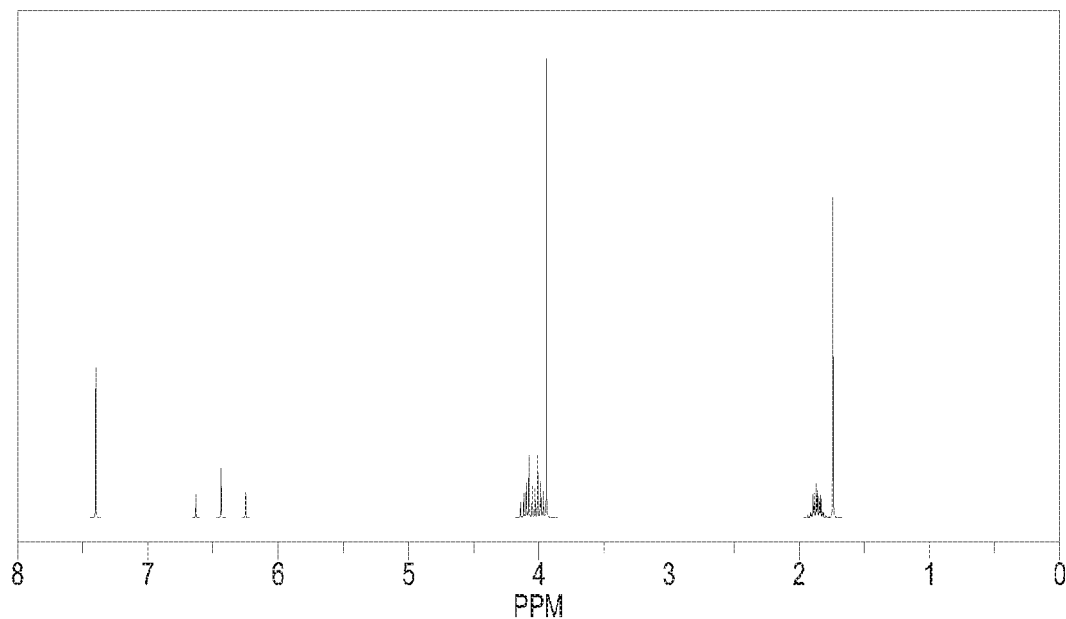
FIG. 13: $^1$H NMR spectrum of 3-(difluoromethyl)-1-methyl-4-(2-methyl-1,3-dioxan-2-yl)-1H-pyrazole.
Figure 14:
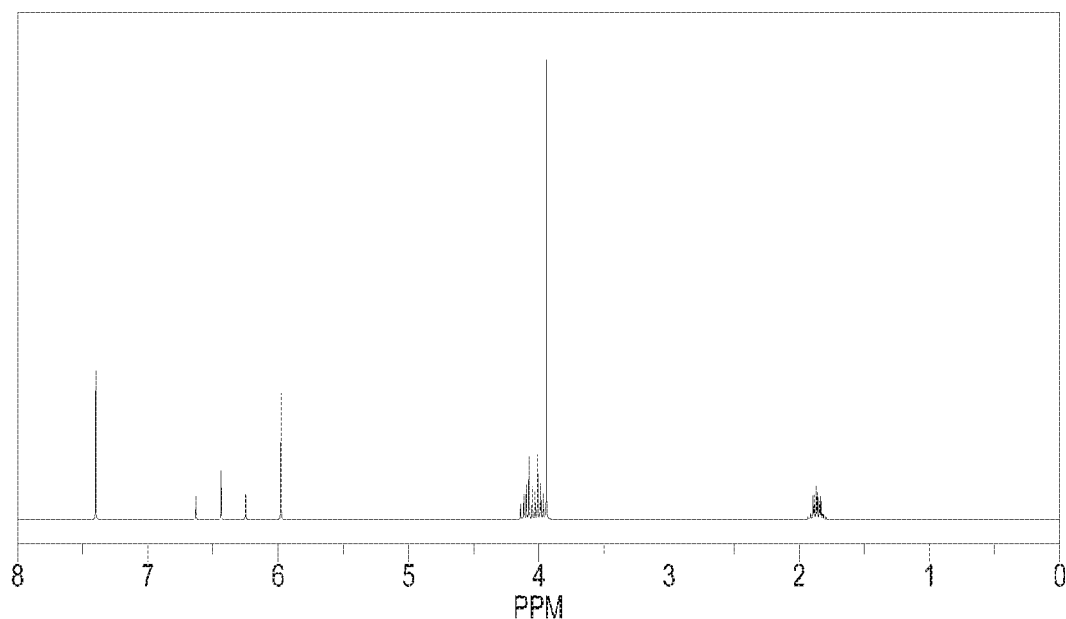
FIG. 14: $^1$H NMR spectrum of 3-(difluoromethyl)-1-methyl-4-(1,3-dioxan-2-yl)-1H-pyrazole.
Figure 15:
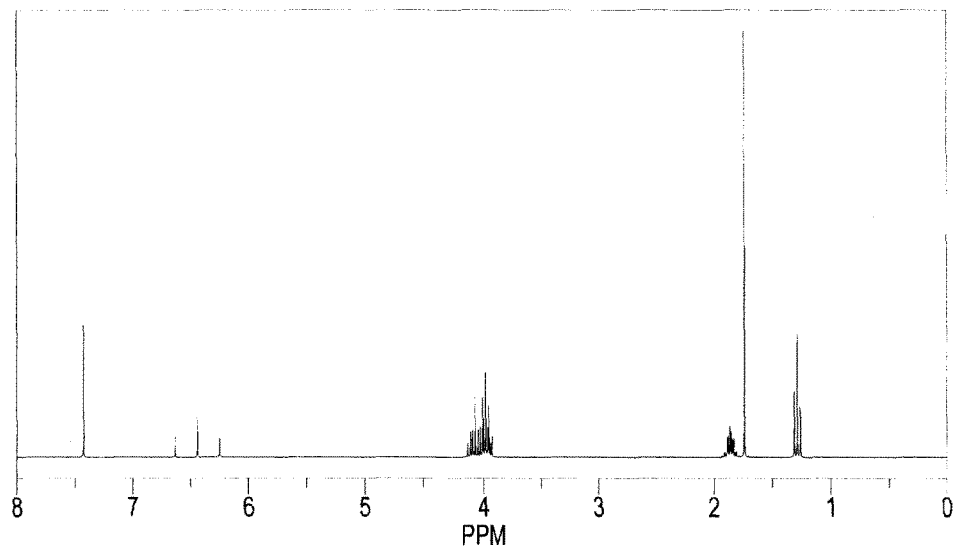
FIG. 15: $^1$H NMR spectrum of 3-(difluoromethyl)-1-ethyl-4-(2-methyl-1,3-dioxan-2-yl)-1H-pyrazole.
Figure 16:
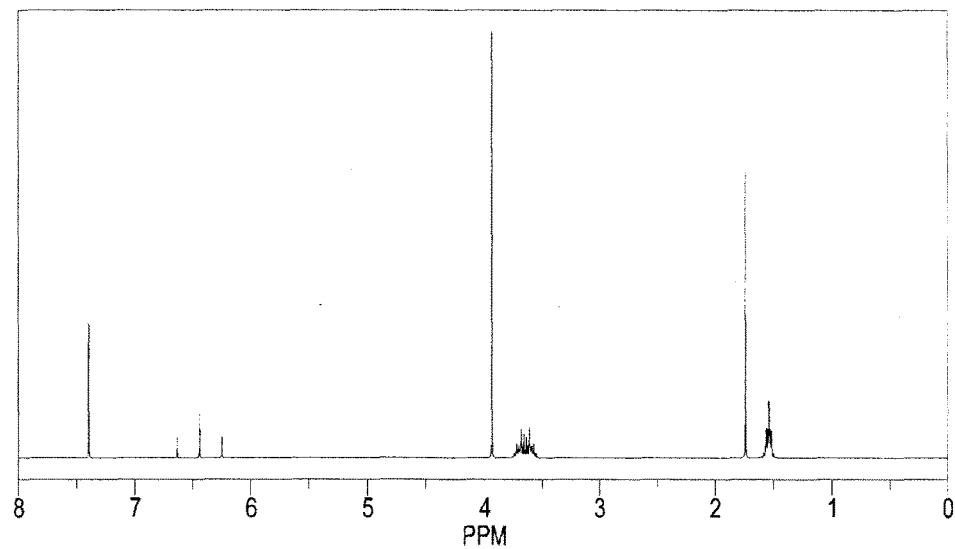
FIG. 16: $^1$H NMR spectrum of 3-(difluoromethyl)-1-methyl-4-(2-methyl-1,3-dioxepan-2-yl)-1H-pyrazole.
Figure 17:
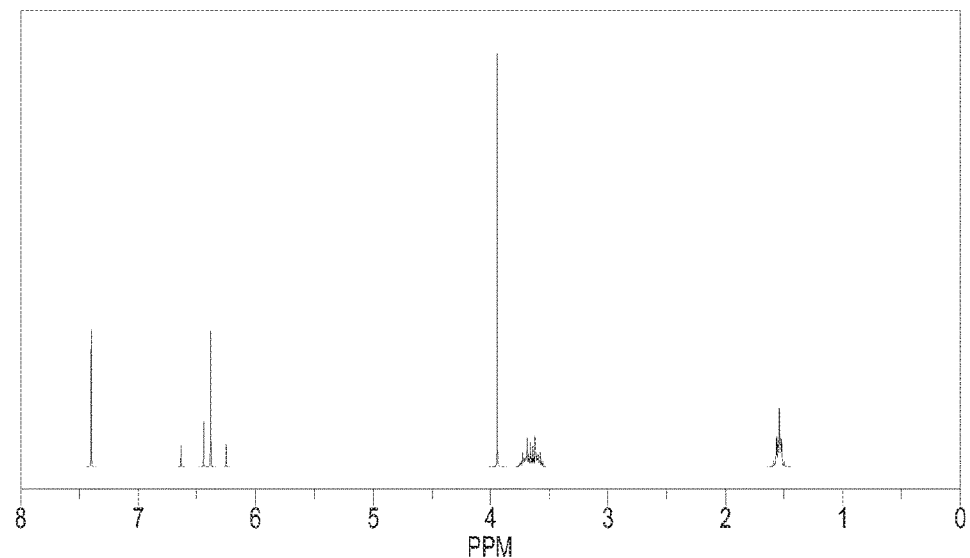
FIG. 17: 1H NMR spectrum of 3-(difluoromethyl)-1-methyl-4-(1,3-dioxepan-2-yl)-1H-pyrazole.
Figure 18:
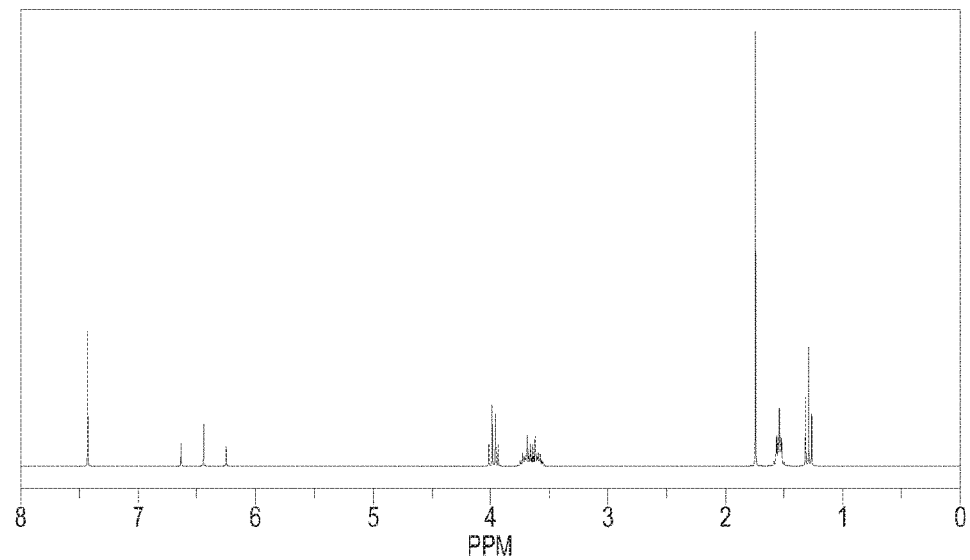
FIG. 18: $^1$H NMR spectrum of 3-(difluoromethyl)-1-ethyl-4-(2-methyl-1,3-dioxepan-2-yl)-1H-pyrazole.

To make the objective, technical solution and advantages of the present invention more apparent, the present invention provides the following embodiments, and they merely serve to explain the present invention, and they can not therefore be construed as limiting the scope of the present invention patent.

It should be noted that any modifications, equivalent replacement and improvement etc., which are made within the spirit and principles of the present invention, should be included within the scope of the present invention.

Example 1: The Preparation Method of 3-(difluoromethyl)-1-methyl-1H-pyrazole-4-carboxylic Acid

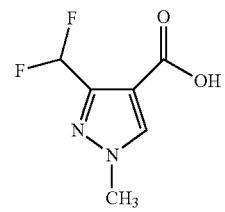

Adding 70 g N-1,1,2,2-tetrafluoro-ethyl dimethyl amine (0.48 mol) and 300 g acetonitrile to a 1000 ml four orifices reaction bulb equipped with a stirring device and a thermometer, and then dropping 150 g $BF_3$ acetonitrile solution into the reaction bulb at 20° C. (wherein, with respect to the amount of N-1,1,2,2-tetrafluoro-ethyl dimethyl amine, containing 1.2 equivalents of $BF_3$), dropwise over 15-30 min, and stirring the reactants in the reaction bulb for 30 min. Dropping 81.8 g (0.58 mol) N,N-dimethyl-2-(2-methyl-1,3-dioxo-2-yl)-vinyl into the reaction bulb dropwise over 30 min. Rising the temperature of the above reaction system gradually to 20° C., and carrying out the reaction in the bulb with heat insulation for 2 hours. Cooling down the temperature of the reaction system to 5° C. after 2 hours heat insulation, and dropping acetonitrile solution of methyl hydrazine (wherein, with respect to the amount of 1,5-diaza pentadiene salt, containing 1.1 equivalents of hydrazine), dropwise over 30 min. Rising the temperature of the reaction system gradually to 20° C. and carrying out the reaction in the bulb with heat insulation for 2 hours. Conducting reduced pressure distillation of the resulting reaction product under 60° C. to recycle acetonitrile. Adding 250 g water with temperature around 50-60° C. to the resulting product. Stirring the resulting mixture slowly and gradually cooling it down to 0° C., meanwhile, crystallization from the resulting mixture is carrying out, and the crystallization period is 1-2 hour. Filtrating the above mixture to obtain crystal, then washing, draining and draying the crystal to obtain 75 g target product. The HPLC-purity of target product is 99.3%, and the yield of this preparation method is 93.3% (the molar yield is calculated with respect to the mole of N-1,1,2,2-tetrafluoro-ethyl dimethyl amine).

Said target product has been analyzed by $^1$H NMR analysis, elemental analysis and mass spectrometry, which could be determined as 3-(difluoromethyl)-1-methyl-4-(2-methyl-1,3-dioxetan-2-yl)-1H-pyrazole, which is one of compound of formula (II).

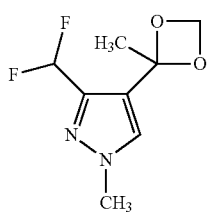

The elemental analysis result and mass spectrometry result of said target product are as follows:

mass spectrometry: m/z: 204.07 (100.0%), 205.07 (9.4%);
elemental analysis: C, 47.06; H, 4.94; F, 18.61; N, 13.72; O, 15.67.

Adding 75 g above compound of formula (II), 300 g water and 100 g 30% hydrochloric acid (0.82 mol) to a 2000 ml four orifices reaction bulb equipped with a stirring device and a thermometer, rising the temperature of this reaction system to 50-60° C. and carrying out hydrolysis reaction for 5 h. Then dropping 480 g 10% sodium hypochlorite solution (0.65 mol), rising the temperature of this reaction system to 100° C., and carrying out reflux reaction for 5 h. After that, cooling the reaction system slowly to 10° C., and crystallizing the resulting product for 2 h. Filtrating the mixture to obtain crystal, then washing, draining and draying the crystal to obtain 57.70 g target product. The HPLC-purity of target product is 99.5%, and the yield of this preparation method is 91.3% (the molar yield is calculated with respect to the mole of above compound of formula (II)). Said target product has been analyzed by $^1$H NMR analysis, elemental analysis and mass spectrometry, which could be determined as 3-(difluoromethyl)-1-methyl-1H-pyrazole-4-carboxylic acid.

Elemental analysis result and mass spectrometry result of said target product are as follows:

mass spectrometry: m/z: 176.04 (100.0%), 177.04 (7.3%);
elemental analysis: C, 40.92; H, 3.43; F, 21.57; N, 15.91; O. 18.17.

Example 2: The Preparation Method of 3-(difluoromethyl)-1-methyl-1H-pyrazole-4-carboxylic Acid

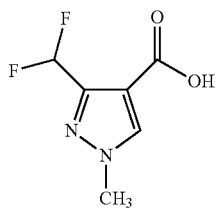

Adding 73 g (0.5 mol) N-1,1,2,2-tetrafluoro-ethyl dimethyl amine and 300 g acetonitrile to a 1000 ml four orifices reaction bulb equipped with a stirring device and a thermometer, and then dropping 180 g BF$_3$ acetonitrile solution into the reaction bulb at 0° C. (wherein, with respect to the amount of N-1,1,2,2-tetrafluoro-ethyl dimethyl amine, containing 1.3 equivalents of BF$_3$), dropwise over 15-30 min, and stirring the reactants in the reaction bulb at room temperature for 30 min. Dropping 78 g (0.55 mol) N,N-dimethyl-2-(2-methyl-1,3-dioxo-2-yl)-vinyl into the reaction bulb, dropwise over 30 min. Carrying out the reaction in the bulb at 30° C. with heat insulation for 2 hours. Cooling down the temperature of the reaction system to 5° C. after 2 hours heat insulation, and dropping acetonitrile solution of methyl hydrazine (wherein, with respect to the amount of 1,5-diaza pentadiene salt, containing 1.1 equivalents of hydrazine), dropwise over 30 min. Rising the temperature of the reaction system gradually to 30° C. and carrying out the reaction in the bulb with heat insulation for 2 hours. Conducting reduced pressure distillation of the resulting reaction product under 60° C. to recycle acetonitrile. Adding 250 g water with temperature around 50-60° C. to the resulting product. Stirring the resulting mixture slowly and gradually cooling it down to 0° C., meanwhile, crystallization from the resulting mixture is carried out, and the crystallization period is 1-2 hour. Filtrating the above mixture to obtain crystal, then washing, draining and draying the crystal to obtain 74.3 g target product. The HPLC-purity of target product is 99.1%, and the yield of this preparation method is 91.6% (the molar yield is calculated with respect to the mole of N-1,1,2,2-tetrafluoro-ethyl dimethyl amine). Said target product has been analyzed by $^1$H NMR analysis, elemental analysis and mass spectrometry, which could be determined as 3-(difluoromethyl)-1-methyl-4-(2-methyl-1,3-dioxetan-2-yl)-1H-pyrazole, which is one of compound of formula (II).

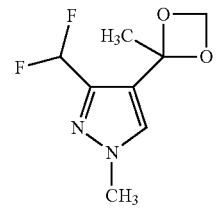

Elemental analysis result and mass spectrometry result of 3-(difluoromethyl)-1-methyl-4-(2-methyl-1,3-dioxetan-2-yl)-1H-pyrazole are as follows:

mass spectrometry: m/z: 204.07 (100.0%), 205.07 (9.4%):
elemental analysis: C, 47.06; H, 4.94; F, 18.61; N, 13.72; O, 15.67.

Adding 74.3 g 3-(difluoromethyl)-1-methyl-4-(2-methyl-1,3-dioxetan-2-yl)-1H-pyrazole, 300 g water and 90 g 30% hydrochloric acid (0.74 mol) to a 1000 ml four orifices reaction bulb equipped with a stirring device and a thermometer, rising the temperature of this reaction system to 50-60° C. and carrying out hydrolysis reaction for 5 h. Then dropping 80 g 30% hydrogen peroxide (0.70 mol), rising the temperature of this reaction system to 100° C., and carrying out reflux reaction for 5 h. After that, cooling the reaction system slowly to 10° C., and crystallizing the resulting product for 2 h. Filtrating the above mixture to obtain crystal, then washing, draining and draying the crystal to obtain 60 g target product. The HPLC-purity of target product is 99.5%, and the yield of this preparation method is 95.2% (the molar yield is calculated with respect to the mole of above compound of formula (II)). Said target product has been analyzed by $^1$H NMR analysis, elemental analysis and mass spectrometry, which could be determined as 3-(difluoromethyl)-1-methyl-1H-pyrazole-4-carboxylic acid.

Example 3: The Preparation Method of 3-(difluoromethyl)-1-methyl-1H-pyrazole-4-carboxylic Acid

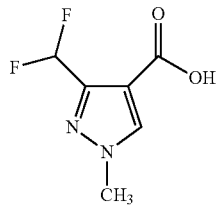

Except using 0.58 mol N,N-dimethyl-2-(1,3-dioxo-2-yl)-vinyl instead of using N,N-dimethyl-2-(2-methyl-1,3-dioxo-2-yl)-vinyl, repeating the preparation method of 3-(difluoromethyl)-1-methyl-4-(2-methyl-1,3-dioxetan-2-yl)-1H-pyrazole in Example 1. Calculating the molar yield with respect to the mole of N-1,1,2,2-tetrafluoro-ethyl dimethyl amine, said molar yield is 90.0%. Said target product has been analyzed by $^1$H NMR analysis, elemental analysis and mass spectrometry, which could be determined as 3-(difluoromethyl)-4-(1,3-dioxetan-2-yl)-1-methyl-1H-pyrazole.

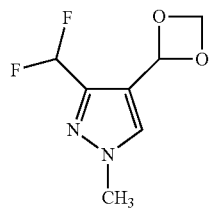

elemental analysis result and mass spectrometry result of said target product are as follows:

mass spectrometry: m/z: 190.06 (100.0%), 191.06 (7.7%);
elemental analysis: C, 44.22; H, 4.24; F, 19.98; N, 14.73; O, 16.83.

Repeating the preparation method of 3-(difluoromethyl)-1-methyl-1H-pyrazole-4-carboxylic acid in Example 1 by using 3-(difluoromethyl)-1-methyl-4-(1,3-dioxetan-2-yl)-1H-pyrazole as intermediate. Using 3-(difluoromethyl)-1-methyl-4-(1,3-dioxetan-2-yl)-1-1H-pyrazole as a benchmark to calculate the molar yield of the method, this yield is obtained as 91.0%. The target product has been analyzed by $^1$H NMR analysis, elemental analysis and mass spectrometry, which could be determined as 3-(difluoromethyl)-1-methyl-1H-pyrazole-4-carboxylic acid.

Example 4: The Preparation Method of 3-(difluoromethyl)-1-methyl-1H-pyrazole-4-carboxylic Acid

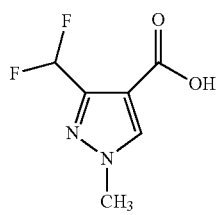

Except using 0.58 mol N,N-dimethyl-2-(1,3-dioxolan-2-yl)-vinyl instead of N,N-dimethyl-2-(2-methyl-1,3-dioxo-2-yl)-vinyl, repeating the preparation method of 3-(difluoromethyl)-1-methyl-4-(2-methyl-1,3-dioxetan-2-yl)-1H-pyrazole in Example 1. Calculating the molar yield with respect to the mole of N-1,1,2,2-tetrafluoro-ethyl dimethyl amine, said molar yield is 90.4%. The target product has been analyzed by $^1$H NMR analysis, elemental analysis and mass spectrometry, which could be determined as 3-(difluoromethyl)-1-methyl-4-(1,3-dioxolan-2-yl)-1H-pyrazole.

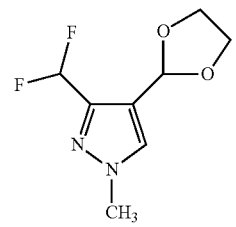

Elemental analysis result and mass spectrometry result of said target product are as follows:

mass spectrometry: m/z: 204.07 (100.0%), 205.07 (9.4%);
elemental analysis: C, 47.06; H, 4.94; F, 18.61; N, 13.72; O, 15.67.

Repeating the preparation method of 3-(difluoromethyl)-1-methyl-1H-pyrazole-4-carboxylic acid in Example 1 by using 3-(difluoromethyl)-1-methyl-4-(1,3-dioxolan-2-yl)-1H-pyrazole as intermediate. Using 3-(difluoromethyl)-1-methyl-4-(1,3-dioxolan-2-yl)-1H-pyrazole as a benchmark to calculate the molar yield of the method, this yield is obtained as 91.4%. The target product has been analyzed by $^1$H NMR analysis, elemental analysis and mass spectrometry, which could be determined as 3-(difluoromethyl)-1-methyl-1H-pyrazole-4-carboxylic acid.

Example 5: The Preparation Method of 3-(difluoromethyl)-1-methyl-1H-pyrazole-4-carboxylic Acid

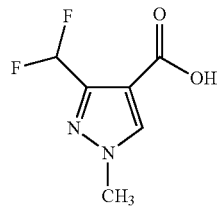

Adding N-1,1,2,2-tetrafluoro-ethyl dimethyl amine 150 g (1.03 mol) and 800 g tetrahydrofuran to a 2000 ml four orifices reaction bulb equipped with a stirring device and a thermometer, and then dropping 350 g BF$_3$ tetrahydrofuran solution at 0° C. (wherein, with respect to the amount of N-1,1,2,2-tetrafluoro-ethyl dimethyl amine, containing 1.3 equivalents of BF$_3$), dropwise over 15-30 min, and stirring the reactants in the reaction bulb at room temperature for 30 min. Dropping 175 g N,N-dimethyl-2-(1,3-dioxolan-2-yl)-vinyl (1.13 mol) into the reaction bulb, dropwise over 30 min. Keeping the reaction temperature at 0° C. for 2 hours. After that, rising the temperature of reaction system to 5° C., and dropping tetrahydrofuran solution of methyl hydrazine (wherein, with respect to the amount of 1,5-diaza pentadiene salt, containing 1.3 equivalents of hydrazine), dropwise over 30 min. Rising the temperature of the reaction system gradually to 20° C., and carrying out the reaction in the bulb with heat insulation for 2 hours. Conducting reduced pressure distillation of the resulting reaction product mixture under 60° C. to recycle tetrahydrofuran until it almost evaporates from the product mixture. Adding 500 g water with temperature around 50-60° C. to the resulting product. Stirring the resulting mixture slowly and gradually cooling it down to 0° C. meanwhile, crystallization from the resulting mixture is carried out, and the crystallization period is 1-2 hour. Filtrating the above mixture to obtain crystal, then washing, draining and draying the crystal to obtain 150 g target product. The HPLC-purity of target product is 99.5%, and the yield of this preparation method is 91.6% (the molar yield is calculated with respect to the mole of N-1,1,2,2-tetrafluoro-ethyl dimethyl amine). Said target product has been analyzed by $^1$H NMR analysis, elemental analysis and mass spectrometry, which could be determined as 3-(difluoromethyl)-4-(1,3-dioxolan-2-yl)-1-methyl-1H-pyrazole, which is one of compound of formula (II).

Equipping a 2000 ml four orifices reaction bulb with a stirring device and a thermometer. Adding 150 g 3-(difluoromethyl)-1-methyl-4-(1,3-dioxolan-2-yl)-1H-pyrazole, 600 g water and 150 g 30% hydrochloric acid (1.23 mol) into the reaction bulb, rising the temperature of this reaction system to 50-60° C. and carrying out hydrolysis reaction for 5 h. Then dropping 150 g 30% hydrogen peroxide (1.32 mol), rising the temperature of this reaction system to 100° C., and carrying out reflux reaction for 5 h. After that, cooling the reaction system slowly to 10° C., and crystallizing the resulting product for 2 h. Filtrating the above mixture to obtain crystal, then washing, draining and draying the crystal to obtain 120 g target product. The HPLC-purity of target product is 99.2%, and the yield of this preparation method is 93.2% (the molar yield is calculated with respect to the mole of above compound of formula (II)). Said target product has been analyzed by $^1$H NMR analysis, elemental analysis and mass spectrometry, which could be determined as 3-(difluoromethyl)-1-methyl-1H-pyrazole-4-carboxylic acid.

Example 6: The Preparation Method of 3-(difluoromethyl)-1-methyl-1H-pyrazole-4-carboxylic Acid

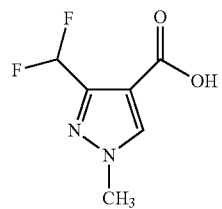

Adding 145 g N-1,1,2,2-tetrafluoro-ethyl dimethyl amine (1.0 mol) and 700 g tetrahydrofuran to a 2000 ml four orifices reaction bulb equipped with a stirring device and a thermometer, and then dropping 350 g BF$_3$ tetrahydrofuran solution at 0° C. (wherein, with respect to the amount of N-1,1,2,2-tetrafluoro-ethyl dimethyl amine, containing 1.3 equivalents of BF$_3$), dropwise over 15-30 min. Stirring the reactants in the reaction bulb at room temperature for 30 min. Then dropping 185 g N,N-dimethyl-2-(2-methyl-1,3-dioxolan-2-yl)-vinyl (1.20 mol) into the reaction bulb, dropwise over 30 min. Keeping the reaction temperature at 0° C. for 2 hours. After that, rising the temperature of reaction system to 5° C., and dropping tetrahydrofuran solution of methyl hydrazine (wherein, with respect to the amount of 1,5-diaza pentadiene salt, containing 1.3 equivalents of hydrazine), dropwise over 30 min. Rising the temperature of the reaction system gradually to 20° C., and carrying out the reaction in the bulb with heat insulation for 2 hours. Conducting reduced pressure distillation of the resulting reaction product under 60° C. to recycle tetrahydrofuran until it almost evaporates from the product mixture. Adding 500 g water with temperature around 50-60° C. to the resulting product. Stirring the resulting mixture slowly and gradually cooling it down to 0° C., meanwhile, crystallization from the resulting mixture is carried out, and the crystallization period lasts for 1-2 hour. Filtrating the above mixture to obtain crystal, then washing, draining and draying the crystal to obtain 155 g target product. The HPLC-purity of target product is 99.5%, and the yield of this preparation method is 93.6% (the molar yield is calculated with respect to the mole of N-1,1,2,2-tetrafluoro-ethyl dimethyl amine). The target product has been analyzed by $^1$H NMR analysis, elemental analysis and mass spectrometry, which could be determined as 3-(difluoromethyl)-1-methyl-4-(2-methyl-1,3-dioxolan-2-yl)-1H-pyrazole.

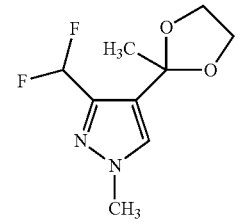

Elemental analysis result and mass spectrometry result of said target product are as follows:
mass spectrometry: m/z: 218.09 (100.0%), 219.09 (9.9%);
elemental analysis: C, 49.54; H, 5.54; F, 17.41; N, 12.84; O, 14.66.

Adding 135 g 3-(difluoromethyl)-1-methyl-4-(2-methyl-1,3-dioxolan-2-yl)-1H-pyrazole, 500 g water and 180 g 30% hydrochloric acid (1.32 mol) to a 3000 ml four orifices reaction bulb equipped with a stirring device and a thermometer, rising the temperature of this reaction system to 50-60° C. and carrying out hydrolysis reaction for 5 h. Dropping 900 g 10% sodium hypochlorite solution (1.21 mol), rising the temperature of this reaction system to 100° C., and carrying out reflux reaction for 5 h. After that, cooling the reaction system slowly down to 10° C., and crystallizing the resulting product for 2 h. Filtrating the above mixture to obtain crystal, then washing, draining and draying the crystal to obtain 118 g target product. The HPLC-purity of target product is 99.3%, and the yield of this preparation method is 91.8%6 (the molar yield is calculated with respect to the mole of above compound of formula (II)). Said target product has been analyzed by $^1$H NMR analysis, elemental analysis and mass spectrometry, which could be determined as 3-(difluoromethyl)-1-methyl-1H-pyrazole-4-carboxylic acid.

Example 7: The Preparation Method of 3-(difluoromethyl)-1-ethyl-1H-pyrazole-4-carboxylic Acid

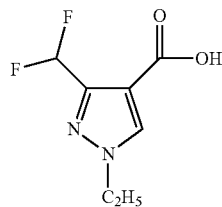

Except using tetrahydrofuran solution of ethyl hydrazine instead of tetrahydrofuran solution of methyl hydrazine, repeating the preparation method of 3-(difluoromethyl)-1-methyl-4-(2-methyl-1,3-dioxolan-2-yl)-1H-pyrazole in the Example 6. Calculating the molar yield with respect to the mole of N-1,1,2,2-tetrafluoro-ethyl dimethyl amine, said molar yield is 90.9%. Said target product has been analyzed by $^1$H NMR analysis, elemental analysis and mass spectrometry, which could be determined as 3-(difluoromethyl)-1-ethyl-4-(2-methyl-1,3-dioxolan-2-yl)-1H-pyrazole, which is as follows:

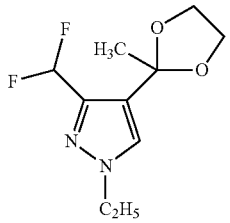 [SMILES: CCn1cc(C2(C)OCCO2)c(C(F)F)n1]

Elemental analysis result and mass spectrometry result of 3-(difluoromethyl)-1-ethyl-4-(2-methyl-1,3-dioxolan-2-yl)-1H-pyrazole are as follows:

mass spectrometry: m/z: 232.10 (100.0%), 233.11 (11.1%);

elemental analysis: C, 51.72; H, 6.08; F, 16.36; N, 12.06; O, 13.78.

Repeating the preparation method of 3-(difluoromethyl)-1-methyl-1H-pyrazole-4-carboxylic acid in Example 6 by using 3-(difluoromethyl)-1-ethyl-4-(2-methyl-1,3-dioxolan-2-yl)-1H-pyrazole as intermediate. Using 3-(difluoromethyl)-1-ethyl-4-(2-methyl-1,3-dioxolan-2-yl)-1H-pyrazole as a benchmark to calculate the molar yield of the method, this yield is obtained as 91.5%. The target product has been analyzed by $^1$H NMR analysis, elemental analysis and mass spectrometry, which could be determined as 3-(difluoromethyl)-1-ethyl-1H-pyrazole-4-carboxylic acid.

Elemental analysis result and mass spectrometry result of said target product are as follows:

mass spectrometry: m/z: 190.06 (100.09%), 191.06 (7.7%);

elemental analysis: C, 44.22; H, 4.24; F, 19.98; N, 14.73; O, 16.83.

Example 8: The Preparation Method of 3-(difluoromethyl)-1-ethyl-1H-pyrazole-4-carboxylic Acid

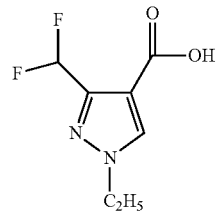 [SMILES: CCn1cc(C(=O)O)c(C(F)F)n1]

Except using tetrahydrofuran solution of ethyl hydrazine instead of using tetrahydrofuran solution of methyl hydrazine, repeating the preparation method of 3-(difluoromethyl)-1-methy-4-(1,3-dioxolan-2-yl)1H-pyrazole in Example 5. Calculating the molar yield with respect to the mole of N-1,1,2,2-tetrafluoro-ethyl dimethyl amine, said molar yield is 90.6%. Said target product has been analyzed by $^1$H NMR analysis, elemental analysis and mass spectrometry, which could be determined as 3-(difluoromethyl)-1-ethyl-4-(1,3-dioxolan-2-yl)-1H-pyrazole, which is as follows:

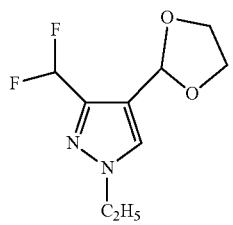

Elemental analysis result and mass spectrometry result of 3-(difluoromethyl)-1-ethyl-4-(1,3-dioxolan-2-yl)-1H-pyrazole are as follows:

mass spectrometry: m/z: 218.09 (100.0%), 219.09 (9.9%);

elemental analysis: C, 49.54; H, 5.54; F, 17.41; N, 12.84; O, 14.66.

Repeating the preparation method of 3-(difluoromethyl)-1-methyl-1H-pyrazole-4-carboxylic acid in Example 5 by using 3-(difluoromethyl)-1-ethyl-4-(1,3-dioxolan-2-yl)-1H-pyrazole as intermediate. Using 3-(difluoromethyl)-1-ethyl-4-(1,3-dioxolan-2-yl)-1H-pyrazole as a benchmark to calculate the molar yield of the method, this yield is obtained as 91.2%. The target product has been analyzed by $^1$H NMR analysis, elemental analysis and mass spectrometry, which could be determined as 3-(difluoromethyl)-1-ethyl-1H-pyrazole-4-carboxylic acid.

Example 9: The Preparation Method of 3-(difluoromethyl)-1-methyl-1H-pyrazole-4-carboxylic Acid

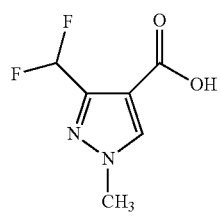

When n=0, R₄=methyl, the corresponding compound of formula (IV) is as follows:

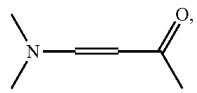

i.e. 4-(dimethylamino)but-3-en-2-one.

Adding 73 g N-1,1,2,2-tetrafluoro-ethyl dimethyl amine (0.5 mol) and 300 g acetonitrile to a 1000 ml four orifices reaction bulb equipped with a stirring device and a thermometer, and then dropping 160 g $BF_3$ acetonitrile solution into the reaction bulb at 20° C. (wherein, with respect to the amount of N-1,1,2,2-tetrafluoro-ethyl dimethyl amine, containing 1.2 equivalents of $BF_3$), dropwise over 15-30 min, stirring the reactants in the reaction bulb for 30 min. Dropping 73.5 g 4-(dimethylamino)but-3-en-2-one (0.65 mol) into the reaction bulb, dropwise over 30 min. Carrying out the reaction in the bulb with heat insulation for 2 hours. Cooling down the temperature of the reaction system to 5° C. after 2 hours heat insulation, and dropping acetonitrile solution of methyl hydrazine (wherein, with respect to the amount of 1,5-diaza pentadiene salt, containing 1.2 equivalents of hydrazine), dropwise over 30 min. Rising the temperature of the reaction system gradually to 20° C., and carrying out the reaction in the bulb with heat insulation for 2 hours. Conducting reduced pressure distillation of the resulting reaction product under 60° C. to recycle acetonitrile. Adding 250 g water with temperature around 50-60° C. to the resulting product. Stirring the resulting mixture slowly and gradually cooling it down to 0° C., meanwhile, crystallization from the resulting mixture is carried out, and the crystallization period lasts for 1-2 hour. Filtrating the above mixture to obtain crystal, then washing draining and draying the crystal to obtain 72 g target product. The HPLC-purity of the target product is 99.3%, and the yield of this preparation method is 90.3% (the molar yield is calculated with respect to the mole of N-1,1,2,2-tetrafluoro-ethyl dimethyl amine). The target product has been analyzed by ¹H NMR analysis, elemental analysis and mass spectrometry, which could be determined as 1-(3-(difluoromethyl)-1-methyl-1H-pyrazol-4-yl)ethanone.

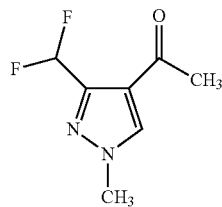

Elemental analysis result and mass spectrometry result of 1-(3-(difluoromethyl)-1-methyl-1H-pyrazol-4-yl)ethanone are as follows:

mass spectrometry: m/z: 174.06 (100.0%), 175.06 (8.3%);
elemental analysis: C, 48.28; H, 4.63; F, 21.82; N, 16.09; O, 9.19.

Adding 72 g above compound of formula (II) to a 2000 ml four orifices reaction bulb equipped with a stirring device and a thermometer, then dropping 500 g 10% sodium hypochlorite solution (0.67 mol) into the reaction bulb, rising the temperature of this reaction system to 100° C., and carrying out reflux reaction for 5 h. After that, cooling the reaction system slowly to 10° C., and crystallizing the resulting product for 2 h. Filtrating the above mixture to obtain crystal, then washing, draining and draying the crystal to obtain 56 g target product. The HPLC-purity of target product is 99.5%, and the yield of this preparation method is 91.3% (the molar yield is calculated with respect to the mole of above compound of formula (II)). Said target product has been analyzed by ¹H NMR analysis, elemental analysis and mass spectrometry, which could be determined as 3-(difluoromethyl)-1-methyl-1H-pyrazole-4-carboxylic acid.

Example 10: The Preparation Method of 3-(difluoromethyl)-1-methyl-1H-pyrazole-4-carboxylic Acid

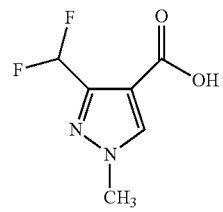

When n=0, R₄=hydrogen, the corresponding compound of formula (IV) is as follows:

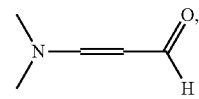

i.e. 3-(dimethylamino)acrylaldehyde.

Adding 145 g N-1,1,2,2-tetrafluoro-ethyl dimethyl amine (1.0 mol) and 700 g acetonitrile into a 2000 ml four orifices reaction bulb equipped with a stirring device and a thermometer, and then dropping 1650 g $BF_3$ acetonitrile solution into the reaction bulb at 20° C. (wherein, with respect to the amount of N-1,1,2,2-tetrafluoro-ethyl dimethyl amine, containing 1.3 equivalents of $BF_3$), dropwise over 15-30 min, and stirring the reactants in the reaction bulb for 30 min. Dropping 120 g 3-(dimethylamino)acrylaldehyde (1.10 mol) into the reaction bulb, dropwise over 30 min. Carrying out the reaction in the bulb with heat insulation for 2 hours. Cooling down the temperature of the reaction system to 5° C. after 2 hours heat insulation, and dropping acetonitrile solution of methyl hydrazine (wherein, with respect to the amount of 1,5-diaza pentadiene salt, containing 1 equivalents of hydrazine), dropwise over 30 min. Rising the temperature of the reaction system gradually to 20° C., and carrying out the reaction in the bulb with heat insulation for 2 hours. Conducting reduced pressure distillation of the resulting reaction product under 60° C. to recycle acetonitrile. Adding 600 g water with temperature around 50-60° C. to the resulting product. Stirring the resulting mixture slowly and gradually cooling it down to 0° C., meanwhile, crystallization from the resulting mixture is carried out, and the crystallization period lasts for 1-2 hour. Filtrating the above mixture to obtain crystal, then washing, draining and draying the crystal to obtain 148 g target product. The HPLC-purity of the target product is 99.3%, and the yield of this preparation method is 92.8% (the molar yield is calculated with respect to the mole of N-1,1,2,2-tetrafluoro-ethyl dimethyl amine). The target product has been analyzed by ¹H NMR analysis, elemental analysis and mass spectrometry, which could be determined as 3-(difluoro methyl)-1-methyl-1H-pyrazole-4-carbaldehyde.

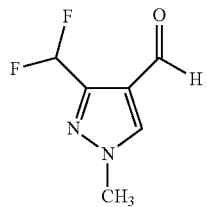

Elemental analysis result and mass spectrometry result of 3-(difluoromethyl)-1-methyl-1H-pyrazole-4-carbaldehyde are as follows:
mass spectrometry: m/z: 160.04 (100.0%), 161.05 (8.3%);
elemental analysis: C, 45.01; H, 3.78; F, 23.73; N, 17.50; O, 9.99.

Adding 148 g above compound of formula (II) into a 3000 ml four orifices reaction bulb equipped with a stirring device and a thermometer, then dropping 1000 g 10% sodium hypochlorite solution (1.34 mol), rising the temperature of this reaction system to 100° C., and carrying out reflux reaction for 5 h. After that, cooling the reaction system slowly to 10° C., and crystallizing the resulting product for 2 h. Filtrating the above mixture to obtain crystal, then washing, draining and draying the crystal to obtain 115 g target product. The HPLC-purity of target product is 99.5%, and the yield of this preparation method is 91.3% (the molar yield is calculated with respect to the mole of above compound of formula (II)). Said target product has been analyzed by $^1$H NMR analysis, elemental analysis and mass spectrometry, which could be determined as 3-(difluoromethyl)-1-methyl-1H-pyrazole-4-carboxylic acid.

Example 11: The Preparation Method of 3-(difluoroethyl)-1-ethyl-1H-pyrazole-4-carboxylic Acid Except using acetonitrile solution of ethyl hydrazine instead of acetonitrile solution of methyl hydrazine, repeating the preparation method of 1-(3-(difluoromethyl)-1-methyl-1H-pyrazol-4-yl)ethanone in the Example 9. Calculating the molar yield with respect to the mole of N-1,1,2,2-tetrafluoro-ethyl dimethyl amine, said molar yield is 91.4%. The target product of the preparation method has been analyzed by $^1$H NMR analysis, elemental analysis and mass spectrometry, which could be determined as 1-(3-(difluoro methyl)-1-ethyl-1H-pyrazol-4-yl)ethanone.

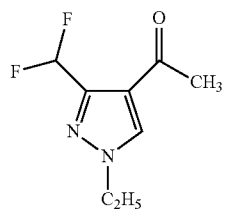

Elemental analysis result and mass spectrometry result of 1-(3-(difluoromethyl)-1-ethyl-1H-pyrazol-4-yl)ethanone are as follows:

mass spectrometry: m/z: 188.08 (100.0%), 189.08 (8.8%);
elemental analysis: C, 51.06; H, 5.36; F, 20.19; N, 14.89; O, 8.50.

Repeating the preparation method of 3-(difluoromethyl)-1-methyl-1H-pyrazole-4-carboxylic acid in the Example 9 by using 1-(3-(difluoromethyl)-1-ethyl-1H-pyrazol-4-yl) ethanone as intermediate. Using 1-(3-(difluoromethyl)-1-ethyl-1H-pyrazol-4-yl)ethanone as a benchmark to calculate the molar yield of the method, this yield is obtained as 91.5%. The target product has been analyzed by $^1$H NMR analysis, elemental analysis and mass spectrometry, which could be determined as 3-(difluoromethyl)-1-ethyl-1H-pyrazole-4-carboxylic acid.

Example 12: The Preparation of 3-(difluoromethyl)-1-ethyl-1H-pyrazole-4-carboxylic Acid Except using acetonitrile solution of ethyl hydrazine instead of using acetonitrile solution of methyl hydrazine, repeating the preparation method of 3-(difluoromethyl)-1-methyl-1H-pyrazole-4-carbaldehyde in the Example 10. Calculating the molar yield with respect to the mole of N-1,1,2,2-tetrafluoro-ethyl dimethyl amine, this yield is obtained as 92.4%. The target product has been analyzed by $^1$H NMR analysis, elemental analysis and mass spectrometry, which could be determined as 3-(difluoromethyl)-1-ethyl-1H-pyrazole-4-carbaldehyde.

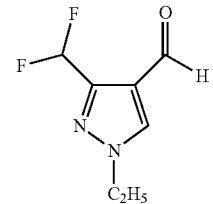

Elemental analysis result and mass spectrometry result of 3-(difluoromethyl)-1-methyl-1H-pyrazole-4-carbaldehyde are as follows:
mass spectrometry: m/z: 1674.06 (100.0%), 175.06 (8.3%);
elemental analysis: C, 48.28; H, 4.63; F, 21.82; N, 16.09; O, 9.19.

Repeating the preparation method of 3-(difluoromethyl)-1-methyl-1H-pyrazole-4-carboxylic acid in the Example 10 by using 3-(difluoromethyl)-1-ethyl-1H-pyrazole-4-carbaldehyde as intermediate. Using 3-(difluoromethyl)-1-ethyl-1H-pyrazole-4-carbaldehyde as a benchmark to calculate the molar yield of the method, this yield is obtained as 94.1%. The target product has been analyzed by $^1$H NMR analysis, elemental analysis and mass spectrometry, which could be determined as 3-(difluoromethyl)-1-ethyl-1H-pyrazole-4-carboxylic acid.

Example 13: The Preparation Method of 3-(difluoromethyl)-1-methyl-1H-pyrazole-4-carboxylic Acid Except using N,N-dimethyl-2-(2-methyl-1,3-dioxohexane-2-yl)-vinyl instead of using N,N-dimethyl-2-(2-methyl-1,3-dioxo-2-yl)-vinyl, repeating the preparation method of 3-(difluoromethyl)-1-methyl-4-(2-methyl-1,3-dioxetan-2-yl)-1H-pyrazole in Example 2. Calculating the molar yield with respect to the mole of N-1,1,2,2-tetrafluoro-ethyl dimethyl amine, said molar yield is 91.9%. The target product has been analyzed by $^1$H NMR analysis elemental analysis and mass spectrometry, which could be determined as 3-(difluoromethyl)-1-methyl-4-(2-methyl-1,3-dioxan-2-yl)-1H-pyrazole, which is as follows:

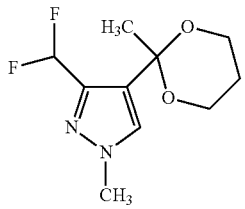

Elemental analysis result and mass spectrometry result of 3-(difluoromethyl)-1-methyl-4-(2-methyl-1,3-dioxan-2-yl)-1H-pyrazole are as follows:
mass spectrometry: m/z: 232.10 (100.0%), 233.11 (11.1%);
elemental analysis: C, 51.72; H, 6.08; F, 16.36; N, 12.06; O, 13.78.

Repeating the preparation method of 3-(difluoromethyl)-1-methyl-1H-pyrazole-4-carboxylic acid in the Example 2 by using 3-(difluoromethyl)-1-methyl-4-(2-methyl-1,3-dioxan-2-yl)-1H-pyrazole as intermediate. Using 3-(difluoromethyl)-1-methyl-4-(2-methyl-1,3-dioxan-2-yl)-1H-pyrazole s a benchmark to calculate the molar yield of the method, this yield is obtained as 92.3%. The target product has been analyzed by $^1$H NMR analysis, elemental analysis and mass spectrometry, which could be determined as 3-(difluoromethyl)-1-methyl-1H-pyrazole-4-carboxylic acid.

Example 14: The Preparation Method of 3-(difluoromethyl)-1-methyl-1H-pyrazole-4-carboxylic acid Except using N,N-dimethyl-2-(1,3-dioxo-hexane-2-yl) vinyl instead of using N,N-dimethyl-2-(1,3-dioxolan-2-yl)-vinyl, repeating the preparation method of 3-(difluoromethyl)-1-methyl-4-(1,3-dioxolan-2-yl)-1H-pyrazole in the Example 5. Calculating the molar yield with respect to the mole of N-1,1,2,2-tetrafluoro-ethyl dimethyl amine said molar yield is 90.9%. Said target product has been analyzed by $^1$H NMR analysis, elemental analysis and mass spectrometry, which could be determined as 3-(difluoromethyl)-4-(1,3-dioxan-2-yl)-1-methyl-1H-pyrazole, which is as follows:

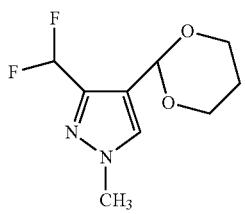

Elemental analysis result and mass spectrometry result of 3-(difluoromethyl)-4-(1,3-dioxan-2-yl)-1-methyl-1H-pyrazole are as follows:
mass spectrometry: m/z: 218.09 (100.0%), 219.09 (9.9%);
elemental analysis: C, 49.54; H, 5.54; F, 17.41; N, 12.84; O, 14.66.

Repeating the preparation method of 3-(difluoromethyl)-1-methyl-1H-pyrazole-4-carboxylic acid in the Example 5 by using 3-(difluoromethyl)-1-methyl-4-(1,3-dioxan-2-yl)-1H-pyrazole as intermediate. Using 3-(difluoromethyl)-1-methyl-4-(1,3-dioxan-2-yl)-1H-pyrazole as a benchmark to calculate the molar yield of the method, this yield is obtained as 91.6%. The target product has been analyzed by $^1$H NMR analysis, elemental analysis and mass spectrometry, which could be determined as 3-(difluoromethyl)-1-methyl-1H-pyrazole-4-carboxylic acid.

Example 15: The Preparation Method of 3-(difluoromethyl)-1-ethyl-1H-pyrazole-4-carboxylic Acid Except using N,N-dimethyl-2-(2-methyl-1,3-dioxohexane-2-yl)-vinyl to replace N,N-dimethyl-2-(2-methyl-1,3-dioxo-2-yl)-vinyl and using tetrahydrofuran solution of ethyl hydrazine to replace acetonitrile solution of methyl hydrazine, repeating the preparation of 3-(difluoromethyl)-1-methyl-4-(2-methyl-1,3-dioxetan-2-yl)-1H-pyrazole in the Example 2. Calculating the molar yield with respect to the mole of N-1,1,2,2-tetrafluoro-ethyl dimethyl amine, said molar yield is 91.6%. The target product has been analyzed by $^1$H NMR analysis, elemental analysis and mass spectrometry, which could be determined as 3-(difluoromethyl)-1-ethyl-4-(2-methyl-1,3-dioxan-2-yl)-1H-pyrazole, which is as follows:

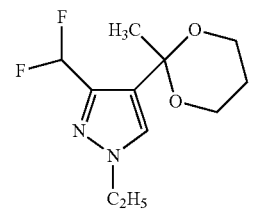 [SMILES: CCn1cc(C2(C)OCCCO2)c(C(F)F)n1]

Elemental analysis result and mass spectrometry result of 3-(difluoromethyl)-1-ethyl-4-(2-methyl-1,3-dioxan-2-yl)-1H-pyrazole are as follows:
mass spectrometry: m/z: 246.12 (100.0° %), 247.12 (12.9%), 248.12 (1.1%);
elemental analysis: C, 53.65; H, 6.55; F, 15.43; N, 11.38; O, 12.99.

Repeating the preparation method of 3-(difluoromethyl)-1-methyl-1H-pyrazole-4-carboxylic acid in the Example 2 by using 3-(difluoromethyl)-1-ethyl-4-(2-methyl-1,3-dioxan-2-yl)-1H-pyrazole as intermediate. Using 3-(difluoromethyl)-1-ethyl-4-(2-methyl-1,3-dioxan-2-yl)-1H-pyrazole as a benchmark to calculate the molar yield of the method, this yield is obtained as 92.2%. The target product has been analyzed by $^1$H NMR analysis, elemental analysis and mass spectrometry; which could be determined as 3-(difluoromethyl)-1-ethyl-1H-pyrazole-4-carboxylic acid.

Example 16: The Preparation Method of 3-(difluoromethyl)-1-methyl-1H-pyrazole-4-carboxylic Acid Except using N,N-dimethyl-2-(2-methyl-1,3-dioxo-heptan-2-yl)-vinyl instead of using N,N-dimethyl-2-(2-methyl-1,3-dioxo-2-yl)-vinyl, repeating the preparation method of 3-(difluoromethyl)-1-methyl-4-(2-methyl-1,3-dioxetan-2-yl)-1H-pyrazole in the Example 2. Calculating the molar yield with respect to the mole of N-1,1,2,2-tetrafluoro-ethyl dimethyl amine, said molar yield is 91.1%. Said target product has been analyzed by $^1$H NMR analysis, elemental analysis and mass spectrometry, which could be determined as 3-(difluoromethyl)-1-methyl-4-(2-methyl-1,3-dioxepan-2-yl)-1H-pyrazole, which is as follows:

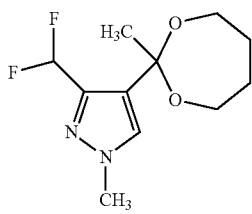 [SMILES: Cn1cc(C2(C)OCCCCO2)c(C(F)F)n1]

Elemental analysis result and mass spectrometry result of 3-(difluoromethyl)-1-methyl-4-(2-methyl-1,3-dioxepan-2-yl)-1H-pyrazole are as follows:

mass spectrometry: m/z: 246.12 (100.0%), 247.12 (12.9%), 248.12 (1.1%);

elemental analysis: C, 53.65; H, 6.55; F, 15.43; N, 11.38; O, 12.99.

Repeating the preparation method of 3-(difluoromethyl)-1-methyl-1H-pyrazole-4-carboxylic acid in the Example 2 by using 3-(difluoromethyl)-1-methyl-4-(2-methyl-1,3-dioxepan-2-yl)-1H-pyrazole as intermediate. Using 3-(difluoromethyl)-1-methyl-4-(2-methyl-1,3-dioxepan-2-yl)-1H-pyrazole as a benchmark to calculate the molar yield of the method, this yield is obtained as 92.0%. The target product has been analyzed by $^1$H NMR analysis, elemental analysis and mass spectrometry, which could be determined as 3-(difluoromethyl)-1-methyl-1H-pyrazole-4-carboxylic acid.

Example 17: The Preparation Method of 3-(difluoromethyl)-1-methyl-1H-pyrazole-4-carboxylic Acid Except using N,N-dimethyl-2-(1,3-dioxo-heptan-2-yl)-vinyl instead of using N,N-dimethyl-2-(1,3-dioxolan-2-yl)-vinyl, repeating the preparation method of 3-(difluoromethyl)-4-(1,3-dioxolan-2-yl)-1-methyl-1H-pyrazole in the Example 5. Calculating the molar yield with respect to the mole of N-1,1,2,2-tetrafluoro-ethyl dimethyl amine, said molar yield is 90.8%. The target product has been analyzed by $^1$H NMR analysis, elemental analysis and mass spectrometry, which could be determined as 3-(difluoromethyl)-1-methy-4-(1,3-dioxepan-2-yl)-1H-pyrazole, which is as follows:

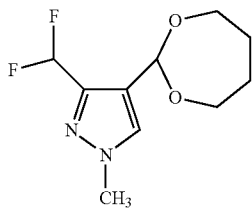 [SMILES: Cn1cc(C2OCCCCO2)c(C(F)F)n1]

Elemental analysis result and mass spectrometry result of 3-(difluoromethyl)-4-(1,3-dioxepan-2-yl)-1-methyl-1H-pyrazole are as follows:

mass spectrometry: m/z: 232.10 (100.0%), 233.11 (11.1%);

elemental analysis: C, 51.72; H, 6.08; F, 16.36; N, 12.06; O, 13.78.

Repeating the preparation method of 3-(difluoromethyl)-1-methyl-1H-pyrazole-4-carboxylic acid in the Example 5 by using 3-(difluoromethyl)-4-1-methyl-(1,3-dioxepan-2-yl)-1H-pyrazole as intermediate. Using 3-(difluoromethyl)-4-1-methyl-(1,3-dioxepan-2-yl)-1H-pyrazole as a benchmark to calculate the molar yield of the method, this yield is obtained as 91.5%. The target product has been analyzed by $^1$H NMR analysis, elemental analysis and mass spectrometry, which could be determined as 3-(difluoromethyl)-1-methyl-1H-pyrazole-4-carboxylic acid.

Example 18: The Preparation Method of 3-(difluoromethyl)-1-ethyl-1H-pyrazole-4-carboxylic Acid Except using N,N-dimethyl-2-(2-methyl-1,3-dioxo-heptan-2-yl)-vinyl to replace N,N-dimethyl-2-(2-methyl-1,3-dioxo-2-yl)-vinyl, and using tetrahydrofuran solution of ethyl hydrazine to replace acetonitrile solution of methyl hydrazine, repeating the preparation method of 3-(difluoromethyl)-1-methyl-4-(2-methyl-1,3-dioxetan-2-yl)-1H-pyrazole in the Example 2. Calculating the molar yield with respect to the mole of N-1,1,2,2-tetrafluoro-ethyl dimethyl amine, said molar yield is 91.7%. The target product has been analyzed by $^1$H NMR analysis, elemental analysis and mass spectrometry, which could be determined as 3-(difluoromethyl)-1-ethyl-4-(2-methyl-1,3-dioxepan-2-yl)-1H-pyrazole, which is as follows:

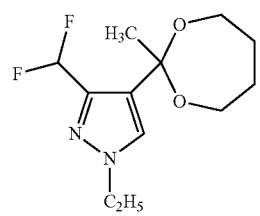 [SMILES: CCn1cc(C2(C)OCCCCO2)c(C(F)F)n1]

Elemental analysis result and mass spectrometry result of 3-(difluoromethyl)-1-ethyl-4-(2-methyl-1,3-dioxepan-2-yl)-1H-pyrazole are as follows:

mass spectrometry: m/z: 260.13 (100.0%), 261.14 (13.3%), 262.14 (1.2%);

elemental analysis: C, 55.37; H, 6.97; F, 14.60; N, 10.76; O, 12.29.

Repeating the preparation method of 3-(difluoromethyl)-1-methyl-1H-pyrazole-4-carboxylic acid in the Example 2 by using 3-(difluoromethyl)-1-ethyl-4-(2-methyl-1,3-dioxepan-2-yl)-1H-pyrazole as intermediate. Using 3-(difluoromethyl)-1-ethyl-4-(2-methyl-1,3-dioxepan-2-yl)-1H-pyrazole as a benchmark to calculate the molar yield of the method, this yield is obtained as 92.1%. The target product has been analyzed by $^1$H NMR analysis, elemental analysis and mass spectrometry, which could be determined as 3-(difluoromethyl)-1-ethyl-1H-pyrazole-4-carboxylic acid.

The invention claimed is:
1. A compound of the following formula (II),

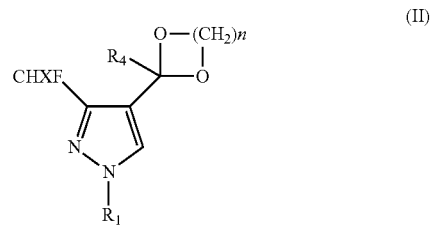

wherein,
R₁ is selected from methyl or ethyl;
R₄ is selected from hydrogen or methyl;
n is 1-4;
X is F, Cl or CF₃.

2. The compound according to claim 1, wherein R₁ is methyl, R₄ is methyl, n is 1, and X is F.

3. A method for preparing the compound of formula (II), said method comprising the following steps of:
(1) in the presence of Lewis acid, reacting α-fluoride amine of formula (III) with ethylene derivative of formula (IV) to obtain vinamidinium salt of formula (V) (i.e. 1,5-diaza-pentadiene salt),
said α-fluoride amine of formula (III) is as follows:

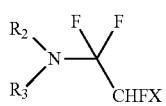

wherein, X is defined as described previously, R₂ and R₃ are independently selected from C₁-C₄ alkyl;
said ethylene derivative of formula (IV) is as follows:

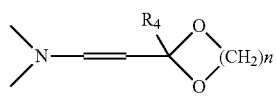

wherein, R₄ is hydrogen or methyl, n is 1-4;
said 1,5-diaza-pentadiene salt of formula (V) is as follows:

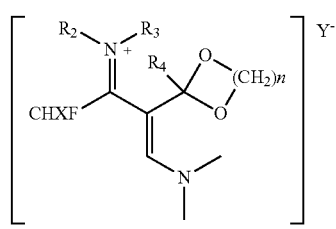

wherein, n, R₂, R₃, and R₄ are defined as described previously, Y⁻ is an anion, said anion is selected from [BF₄]⁻, [AlCl₃F]⁻, [AlF₄]⁻, [ZnCl₂F]⁻, [SbF₆]⁻, [SnCl₄F]⁻, [BiCl₃F]⁻, [GaCl₃F]⁻ and [SiCl₄F]⁻, which are derived from the corresponding Lewis acids;
(2) reacting the 1,5-diaza-pentadiene salt of formula (V) with hydrazine to obtain the compound of formula (II).

4. A method for preparing compound of formula (I), said compound of formula (I) is as follows,

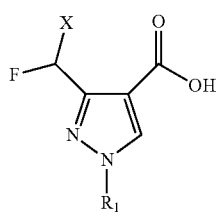

wherein, R₁ is methyl or ethyl;
X is F, Cl or CF₃;

said method comprising the following steps of:
(1) in the presence of Lewis acid, reacting α-fluoride amine of formula (III) with ethylene derivative of formula (IV) to obtain vinamidinium salt of formula (V) (i.e. 1,5-diaza-pentadiene salt),
said α-fluoride amine of formula (III) is as follows:

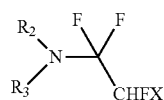

wherein, X is defined as described previously, and R₂ and R₃ are independently selected from C₁-C₄ alkyl;
said ethylene derivative of formula (IV) is as follows:

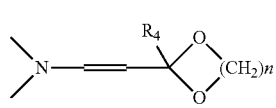

wherein, R₄ is hydrogen or methyl, and n is 1-4;
said 1,5-diaza-pentadiene salt of formula (V) is as follows:

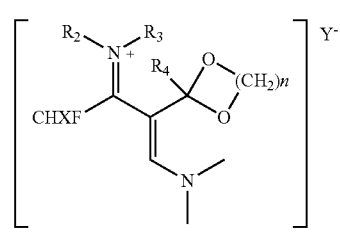

wherein, n, R₂, R₃, and R₄ are defined as described previously, and Y⁻ is an anion, said anion is selected from [BF₄]⁻, [AlCl₃F]⁻, [AlF₄]⁻, [ZnCl₂F]⁻, [SbF₆]⁻, [SnCl₄F]⁻, [BiCl₃F]⁻, [GaCl₃F]⁻ and [SiCl₄F]⁻;
(2) reacting the 1,5-diaza-pentadiene salt of formula (V) with hydrazine to obtain the compound of formula (II),
said compound of formula (II) is as follows:

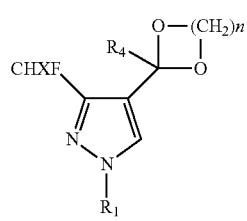

wherein, X, n, R₁, and R₄ are defined as described previously;
(3) hydrolyzing and oxidizing one of the compounds of formula (II) with n=1-4 to obtain the compound of formula (I).

5. The method according to claim 3, wherein, the Lewis acid in step (1) is selected from the following compounds:

$BF_3$, $AlCl_3$, $AlF_3$, $ZnCl_2$, $PF_5$, $SbF_5$, $SnCl_4$, BiCl, $GaCl_3$ and $SiCl_4$ with the molar ratio of the Lewis acid and the α-fluoride amine is 1:1 to 10:1.

6. The method according to claim 3, wherein the reaction temperatures in step (1) and step (2) are around −20° C. to 60° C.

7. The method according to claim 3, wherein the reaction in step (2) is carried out in the presence of solvent, said solvent is selected from diethyl ether, acetonitrile, methylene chloride and tetrahydrofuran.

8. The method according to claim 3, wherein, the hydrazine used in step (2) is methylhydrazine or ethylhydrazine.

9. The method according to claim 3, wherein, the molar ratio of 1,5-diaza-pentadiene salt of formula (V) and hydrazine in step (2) is 1:10 to 10:1.

10. The method according to claim 3, wherein the hydrolyzing reaction of compound of formula (II) in step (3) is carried out in the presence of solvent, said solvent is selected from mixture of methanol, ethanol, acetonitrile, or tetrahydrofuran, with water or using water alone as a solvent.

11. The method according to claim 3, wherein the hydrolysis reaction of compound of formula (II) in step (3) is carried out in the presence of acid, said acid is hydrochloric acid, sulfuric acid, hydrobromic acid or phosphoric acid, the molar ratio of compound of formula (II) and acid is 1:2 to 1:10.

12. The method according to claim 3, wherein the oxidizing agent used in step (3) is selected from hydrogen peroxide, sodium hypochlorite, potassium permanganate, sodium chlorate, potassium chlorate, the temperature of oxidation reaction is around 30° C. to 100° C.

13. The method according to claim 3, wherein the hydrolysis reaction and the oxidation reaction in step (3) are continuously carried out, the molar ratio of compound of formula (II) and oxidizing agent is 1:2 to 1:10.

14. The method according to claim 5, wherein the Lewis acid in step (1) is $BF_3$, with the molar ratio of the Lewis acid and the α-fluoride amine is 1:1 to 5:1.

15. The method according to claim 5, wherein the molar ratio of the Lewis acid and the α-fluoride amine in step (1) is 1:1 to 1.3:1.

16. The method according to claim 6 wherein the reaction temperatures in step (1) and step (2) are around −10° C. to 40° C.

17. The method according to claim 6, wherein the reaction temperatures in step (1) and step (2) are around 0° C. to 30° C.

18. The method according to claim 9, wherein the molar ratio of 1,5-diaza-pentadiene salt of formula (V) and hydrazine in step (2) is 1:5 to 5:1.

19. The method according to claim 9, wherein the molar ratio of 1,5-diaza-pentadiene salt of formula (V) and hydrazine in step (2) is 1.3:1 to 1:1.3.

20. The method according to claim 12, wherein the oxidizing agent used in step (3) is hydrogen peroxide or sodium hypochlorite, and the temperature of oxidation reaction is around 50° C. to 100° C.

* * * * *